US008273360B2

(12) United States Patent
Pizza et al.

(10) Patent No.: US 8,273,360 B2
(45) Date of Patent: Sep. 25, 2012

(54) **OUTER MEMBRANE VESICLE (OMV) VACCINE COMPRISING *N. MENINGITIDIS* SEROGROUP B OUTER MEMBRANE PROTEINS**

(75) Inventors: Mariagrazia Pizza, Siena (IT); Rino Rappuoli, Siena (IT); Marzia Monica Giuliani, Siena (IT)

(73) Assignee: Novartis AG, Basel (CH)

( * ) Notice: Subject to any disclaimer, the term of this patent is extended or adjusted under 35 U.S.C. 154(b) by 1662 days.

(21) Appl. No.: 10/181,600

(22) PCT Filed: Jan. 17, 2001

(86) PCT No.: PCT/IB01/00166
§ 371 (c)(1),
(2), (4) Date: Mar. 31, 2003

(87) PCT Pub. No.: WO01/52885
PCT Pub. Date: Jul. 26, 2001

(65) Prior Publication Data
US 2004/0249125 A1 Dec. 9, 2004

(30) Foreign Application Priority Data

Jan. 17, 2000 (GB) .................................. 0001067.8
Mar. 9, 2000 (GB) .................................. 0005699.4

(51) Int. Cl.
*A61K 39/095* (2006.01)
*A61K 39/02* (2006.01)
*A61K 39/116* (2006.01)
*A61K 39/00* (2006.01)
*A61K 38/00* (2006.01)
*C07K 1/00* (2006.01)
*C07K 14/00* (2006.01)

(52) U.S. Cl. ............... 424/250.1; 424/234.1; 424/184.1; 424/190.1; 424/203.1; 530/350; 530/300; 530/825; 514/1.1

(58) Field of Classification Search ............... 424/203.1, 424/234.1, 184.1, 250.1; 514/2; 530/350, 530/825
See application file for complete search history.

(56) References Cited

U.S. PATENT DOCUMENTS

| 6,048,527 | A * | 4/2000 | Granoff et al. ............. 424/150.1 |
| 6,180,111 | B1 | 1/2001 | Stein et al. |
| 6,355,253 | B1 * | 3/2002 | Zlotnick ..................... 424/234.1 |
| 6,451,317 | B1 | 9/2002 | Blake et al. |
| 7,018,636 | B1 | 3/2006 | Bhattacharjee et al. |
| 7,118,757 | B1 * | 10/2006 | Seid et al. .................. 424/250.1 |
| 7,576,176 | B1 * | 8/2009 | Fraser et al. ..................... 530/350 |
| 7,785,608 | B2 * | 8/2010 | Zlotnick et al. ............. 424/249.1 |
| 2004/0092711 | A1 | 5/2004 | Arico |
| 2004/0110670 | A1 | 6/2004 | Arico et al. |
| 2004/0167068 | A1 * | 8/2004 | Zlotnick et al. ................... 514/12 |
| 2005/0222385 | A1 | 10/2005 | Pizza |
| 2006/0029621 | A1 | 2/2006 | Granoff et al. |
| 2006/0051840 | A1 | 3/2006 | Arico et al. |
| 2006/0171957 | A1 | 8/2006 | Pizza |
| 2007/0026021 | A1 * | 2/2007 | Fraser et al. ............. 424/250.1 |
| 2007/0082014 | A1 | 4/2007 | Costantino |
| 2008/0241180 | A1 | 10/2008 | Contorni |
| 2009/0232820 | A1 | 9/2009 | Fraser et al. |
| 2009/0285845 | A1 | 11/2009 | Masignani |

FOREIGN PATENT DOCUMENTS

| EP | 0011243 | 5/1980 |
| EP | 0467714 | 1/1992 |
| WO | WO 95/03413 A1 | 2/1995 |
| WO | WO 96/29412 A1 | 9/1996 |
| WO | WO 97/28273 A1 | 8/1997 |
| WO | WO-9817805 | 4/1998 |
| WO | WO 99/24578 A2 | 5/1999 |
| WO | WO 99/31132 A1 | 6/1999 |
| WO | WO 99/36544 A2 | 7/1999 |
| WO | WO 99/55873 A2 | 11/1999 |
| WO | WO 99/57280 A2 | 11/1999 |
| WO | WO 99/58683 A2 | 11/1999 |
| WO | WO 99/61053 A1 | 12/1999 |
| WO | WO-0022430 | 4/2000 |
| WO | WO-00/25811 | 5/2000 |
| WO | WO 00/66791 A1 | 11/2000 |
| WO | WO-01/34642 | 5/2001 |
| WO | WO-0131019 | 5/2001 |
| WO | WO 0152885 | * 7/2001 |
| WO | WO 0164920 | * 9/2001 |
| WO | WO-0164922 | 9/2001 |
| WO | WO-02/09643 | 2/2002 |
| WO | WO-03020756 | 3/2003 |
| WO | WO-03/063766 | 8/2003 |
| WO | WO-2004/019977 | 3/2004 |
| WO | WO-2004032958 | 4/2004 |
| WO | WO-2004048404 | 6/2004 |
| WO | WO-2005/004908 | 1/2005 |
| WO | WO-2006024954 | 3/2006 |
| WO | WO-2006/081259 | 8/2006 |

OTHER PUBLICATIONS

Dunn et al. Microbial Pathogenesis 18: 81-96, 1995.* Welsch et al. J. Immunol. 172: 5606-5615, 2004.*
Fredriksen et al. NIPH Annals 14: 67-69, 1991.*
Koeberling et al. Vaccine 25: 1912-1920, 2007.*
Beernink et al. Clin. Vaccine Immunol. 13: 758-763, Jul. 2006.*
Tolman et al. Int. J. Peptide Protein Res. 41: 455-466, 1993.*
McGuinnes et al. Lancet 337: 514-517, Mar. 1991.*
McGuinnes et al. Mol. Microbiol. 7: 505-514, Feb. 1993.*
Colman PM. Research Immunol. 145: 33-36, 1994.*
Cruse et al., Illustrated Dictionary of Immunology, 2nd Edn., CRC Press, 2003.*
Haneberg et al. Infect. Immun. 66: 1334-1341, 1998.*
Gomez et al. Vaccine 14: 1340-1346, 1996.*
Malorny et al. J. Bacteriol. 180: 1323-1330, 1998.*
Teerlink et al. J. Exp. Med. 166: 63-76, 1987, abstract.*
Forest et al. Gene 192: 165-169, 1997.*
Ala'Aldeen et al. Vaccine 12: 535-541, 1994, abstract.*
Greenspan et al. Nature Biotechnology 17:936-937, 1999.*
Bjune et al., "Effect of outer membrane vesicle vaccine against group B meningococcal disease in Norway," *Lancet* 338(8775):1093-1096, 1991.

(Continued)

*Primary Examiner* — S. Devi
(74) *Attorney, Agent, or Firm* — Amy Hessler; Otis Littlefield

(57) ABSTRACT

A composition comprising (a) *Neisseria meningitidis* serogroup B outer membrane vesicles (OMVs), and (b) an immunogenic component selected from other *Neisseria* proteins, or immunogenic fragments thereof. Component (b) preferably includes a protein from a different NmB strain from that from which the OMV of component (a) is derived. The OMVs are preferably obtained by deoxycholate extraction. Optionally, the composition may also comprise a protective antigen against other pathogens.

17 Claims, No Drawings

OTHER PUBLICATIONS

Claassen et al., "Production, characterization and control of a *Neisseria meningitidis* hexavalent class 1 outer membrane protein containing vesicle vaccine," *Vaccine* 14(10):1001-1008, 1996.

Corbel, "Control testing of combined vaccines: a consideration of potential problems and approaches," *Biologicals* 22(4):353-360, 1994.

Lieberman et al., "Safety and immunogenicity of a serogroups A/C *Neisseria meningitidis* oligosaccharide-protein conjugate vaccine in young children," *JAMA* 275(19):1499-1503, 1996.

Manning et al., "OMP85 Proteins of *Neisseria gonorrhoeae* and *Neisseria meningitidis* are similar to *Haemophilus influenzae* D-15-AG and *Pasteurella multocida* OMA87," *Microbial Pathogenesis* 25(1):11-21, 1998.

Nassif et al., "Roles of pilin and PilC in adhesion of *Neisseria meningitidis* to human epithelial and endothelial cells," *Proc. Natl. Aca. Sci. USA* 91(9):3769-3773, 1994.

Parkhill et al., "Complete DNA sequence of a serogoup A strain of *Neisseria meningitidis* Z2491," *Nature* 404:502-506, 2000.

Peeters et al., "Phase I clinical trial with a hexavalent PorA containing meningococcal outer membrane vesicle vaccine," *Vaccine* 14(10):1009-1015, 1996.

Peltola, "Prophylaxis of bacterial meningitis," *Infectious Disease Clinics of North America* 13(3):685-710, 1999.

Romero et al., "Current status of Meningococcal group B vaccine candidates: capsular or noncapsular?" *Clin. Microbiol. Rev.* 7(4):559-575, 1994.

Schuchat et al., "Bacterial meningitis in the United States in 1995," *N. Engl. J. Med.* 337(14):970-976, 1997.

Tettelin et al., "Complete genome sequence of *Neisseria meningitidis* serogroup B strain MC58," *Science* 287:1809-1815, 2000.

Van Der Ley et al., "Construction of *Neisseria meningitidis* strains carrying multiple chromosomal copies of the porA gene for use in the production of a multivalent outer membrane vesicle vaccine," *Vaccine* 13(4):401-407, 1995.

Database accession No. NMB1994.Tettelin et al. (Mar. 2, 2010).

International Preliminary Examination Report mailed Aug. 23, 2000, for international patent application No. PCT/US99/11977, filed May 28, 1999.

Rosenqvist et al. (1998). "Effect of Aluminum Hydroxide and Meningococcal Serogroup C Capsular Polysaccharide on the Immunogenicity and Reactogenicity of a Group B *Neisseria meningitidis* Outer Membrane Vesicle Vaccine," Developments in Biological Standardization, vol. 92, pp. 323-333.

Hou et al. (2005). "Protective Antibody Responses Elicited by a Meningococcal Outer Membrane Vesicle Vaccine with Overexpressed Genome-Derived Neisserial Antigen 1870," J Infect Dis 192(4):580-90.

Katial et al. (2002). "Immunogenicity and Safety Testing of a Group B Intransal Meningococcal Native Outer Membrane Vesicle Vaccine," Infection and Immunity 70(2):702-707.

Zhu et al. (2005). "Evaluation of Recombinant Lipidated P2086 Protein as a Vaccine Candidate for Group B *Neisseria meningitidis* in a Murine Nasal Challenge Model," Infect Immun 73(10):6838-45.

1997-11-17-NM_shotgun.dbs and 1997-12-15-NM.dbs, located at <ftp://ftp.sanger.ac.uk/pub/pathogens/nm/old data/>.

Aasel et al. (1998). Abstract from the 11th International Pathogenic *Neisseria* Conference, Nice France, Nov. 1-6, 1998. pp. 37-38.

Bernfield L. et al. (Sep. 2002). "Identification of a novel vaccine candidate for group B *Neisseria meningitidis*," Thirteenth International Pathogenic *Neisseria* Conference, Norwegian Institute of Public Health, Oslo, Norway, pp. 116.

Boslego et al. (1991). "Gonorrhea Vaccines," Chapter 17 in Vaccines and Immunotherapy, Cryz S.J. (Ed.), Pergamon Press: New York, NY, pp. 211-223.

Cannon (1989). "Conserved Lipoproteins of Pathogenic *Neisseria* Species Bearing the H.8 Epitope: Lipid-Modified Azurin and H.8 Outer Membrane Protein," Clinical Microbiology Reviews, vol. 2, Suppl., S1-S4.

Cantini et al. (Mar. 2006). "Solution Structure of the Immunodominant Domain of Protective Antigen GNA 1870 of *Neisseria meningitidis*," Journal of Biological Chemistry 281(11): 7220-7227.

Declaration by Dr. Julian Parkhill dated Jun. 12, 2008. 2 pages.

Farley J. et al. (Sep. 2002). "Characterization, cloning and expression of different subfamilies of the ORF 2086 gene from *Neisseria meningitidis*," Thirteenth International Pathogenic *Neisseria* Conference, Norwegian Institute of Public Health, Oslo, Norway, p. 124.

Feavers et al. (2009). "Meningococcal protein antigens and vaccines," Vaccine 275:B42-B50.

Fleischmann et al. (1995). "Whole-Genome Random Sequencing and Assembly of *Haemophilus influenzae* Rd," Science 269:496-501.

Fletcher et al. (2004). "Vaccine Potential of the *Neisseria meningitidis* 2086 Lipoprotein," Infection and Immunity 72(4): 2088-2100.

Fontana et al. (2002). "A genomic approach to identify vaccine candidates against gonococcus." Abstract from the 13th International Pathogenic *Neisseria* Conference, Oslo, Norway, Sep. 1-6, 2002. p. 248.

Giuliani et al. (2006). "A universal vaccine for serogroup B meningococcus," PNAS 103(29):10834-10839.

Giuliani et al. (Feb. 2005). "The Region Comprising Amino Acids 100 to 255 of *Neisseria meningitidis* Lipoprotein GNA 1870 Elicits Bactericidal Antibodies," Infection and Immunity 73(2): 1151-1160.

JCVI-CMR website showing Z2491 Sanger sequence (http://cmr.jcvi.org/tigr-scripts/CMR/shared/Genomes.cgi and links).

Masignani V. (Mar. 17. 2003). "Vaccination against *Neisseria meningitidis* using three variants of the lipoprotein GNA1870," J. Exp. Med. 197(6):789-799.

Morley, S. et al. (Dec. 12, 2001). "Vaccine prevention of meningococcal disease, coming soon?" Vaccine 20(5-6):666-687.

Nassif (2000). "A Furtive Pathogen Revealed," Science 287: 1767-1768.

Phase II clinical results for Novartis vaccine, Oct. 9, 2008.

Pizza et al. (2000). "Identification of Vaccine Candidates Against Serogroup B Meningococcus by Whole-Genome Sequencing," Science 287(5459):1816-1820.

Post by Dr. Parkhill on BIOSCl/Bionet of May 8, 1998.

PSORT analysis of 200 of the sequences disclosed in PCT/US99/09346 (1 i.e., the original application underlying the Patent; published as WO99/057280.

Response to Communication, filed in EP Application No. 07075161.5. Oct. 28, 2009.

Rinaudo et al. (2009). "Vaccinology in the genome era", The Journal of Clinical Investigation, 119(9):2515-2525.

Romero et al. (1994). "Current status of Meningococcal group B vaccine candidates: capsular or noncapsular?" Clin. Microbiol. Rev. 7(4):559-575.

Sanger Centre's "Projects" website as of Dec. 10, 1997 as retrievable via http://web.archive.org.

Sequence for "Putative Lipoprotein [*Neisseria meningitidis* Z2491]," NCBI Reference Sequence: YP_002342062.1, Mar. 30, 2000.

Serruto et al. (2009). "Genome-based approaches to develop vaccines against bacterial pathogens," Vaccine 27:3245-3250.

Supplementary Declaration by Dr. Julian Parkhill, dated May 10, 2010.

Telford et al. (2003). "Genomic and Proteomics in Vaccine Design," in New Bacterial Vaccines, edited by Ellis et al. Kleweur Academic/Plenum Publishers, USA. pp. 1-11 (2 pages).

U.S. Appl. No. 60/098,685, "*Neisseria* Spp, Polypeptide, Gene Sequence and Uses Thereof," filed Sep. 1, 1998.

Zollinger (1997). "New and Improved Vaccines Against Meningococcal Disease" in New Generation Vaccines, 2nd Ed., edited by Levine et al., Marcel Dekker, New York. pp. 469-488.

Notice of Opposition against European Patent EP 1645631, granted on Oct. 24, 2007. Opposition filed on Jul. 23, 2008. 20 pages.

Supplemental Submission in Opposition against European Patent EP 1645631, granted on Oct. 24, 2007. Opposition filed on May 25, 2010. 28 pages.

Patentees' Response to Opposition against European Patent EP 1645631, granted on Oct. 24, 2007. 13 pages.

\* cited by examiner

SEQUENCE LISTING

<160> NUMBER OF SEQ ID NOS: 22

<210> SEQ ID NO 1
<211> LENGTH: 15
<212> TYPE: PRT
<213> ORGANISM: Neisseria meningitidis

<400> SEQUENCE: 1

Asp Phe Thr Ile Gln Asp Ile Arg Val Glu Gly Leu Gln Arg Thr
 1               5                  10                  15

<210> SEQ ID NO 2
<211> LENGTH: 2394
<212> TYPE: DNA
<213> ORGANISM: Neisseria meningitidis

<400> SEQUENCE: 2

```
atgaaactga aacagattgc ttccgcactg atgatgttgg gcatatcgcc tttggcactt      60
gccgacttca ccatccaaga catccgcgtc gaaggcttgc agcgtaccga gccgagtacc     120
gtattcaact acctgccgt caaagtcggc gacacctaca cgacacaca cggcagtgcc      180
atcatcaaaa gcctgtacgc caccggtttc tttgacgacg tacgcgtcga aactgcggac     240
gggcagctcc tgctgaccgt tatcgaacgc cccaccatcg gctcgctcaa catcaccggc     300
gcaaaaatgc tgcaaaacga cgccattaag aaaaacctcg aatcgttcgg gctggcgcag     360
tcgcaatact ttaatcaggc gacactcaat caggcagtcg ccggcctgaa agaagaatac     420
ctcgggcgcg gcaaactcaa tatccaaatc acgcccaaag taaccaaact cgcccgcaac     480
cgcgtcgaca tcgacatcac gattgacgag ggcaaatccg ccaaaatcac cgacatcgaa     540
tttgaaggca ccaagtcta ttccgaccgc aaactgatgc ggcaaatgtc cctgaccgaa     600
ggcggcattt ggacatggct gacacgaagc aaccaattca cgagcagaa atttgcccaa     660
gatatggaaa agtaaccga cttctaccaa ataacggct acttcgattt ccgtatcctc     720
gataccgaca tccaaaccaa cgaagacaaa accaagcaga ccatcaaaat caccgtccac     780
gaaggcggac gtttccgttg gggcaaagtc tccatcgaag gcgacaccaa cgaagtcccc     840
aaagccgaac tggaaaaact gctgaccatg aagcccggca atggtacga acgccagcag     900
atgaccgccg ttttgggtga gattcagaac cgcatgggct cggcaggcta cgcatacagc     960
gaaatcagcg tacagccgct gccgaacgct gaaaccaaaa ccgtcgattt cgtcctgcac    1020
atcgaaccgg gccggaaaat ctacgtcaac gaaatacaca tcaccggcaa caacaaaacc    1080
cgcgacgaag tcgtccgccg tgaattacgc caaatggaat ccgcaccta cgacacctcc    1140
aagctgcaac gttccaaaga gcgcgtcgag cttttgggct acttcgacaa tgtccagttt    1200
gatgctgtcc cgcttgccgg cacgcccgac aaagtcgatt tgaacatgag tctgaccgaa    1260
cgttccaccg gttccctgga tttgagcgcg ggttgggttc aagataccgg gttggtcatg    1320
tccgcaggcg tttcccaaga caacctgttc ggtacgggca gtcggccgc actgcgcgcc    1380
tccaggagca aaaccacgct taacggctcg ctgtcgttta ctgacccgta cttcacggca    1440
gacggggtca gcctgggcta cgatgtttac ggaaaagcct tcgacccgcg caaagcatcg    1500
accagcatca acaatataa aaccaccacg gcaggcgcag gcatccgcat gagcgtgcct    1560
gttaccgaat cgaccgcgt gaatttcggt ttggtggcag aacacctgac cgtcaacacc    1620
tacaacaaag cgcccaaaca ctatgccgac tttatcaaga aatacggcaa accgacggc    1680
acagacggca gcttcaaagg ctggctgtac aaaggtaccg tcggctgggg cgcaacaaa    1740
```

```
accgacagcg cgttatggcc gacgcgcggc tacctgacgg gcgtgaacgc cgaaatcgcc    1800
ctgcctggca gcaaactgca atactactcc gccacccaca accaaacctg gttcttcccc    1860
ctgagcaaaa ccttcacgct gatgctcggc ggcgaagtcg gcattgcggg cggctacggc    1920
agaaccaaag aaatccccctt ctttgaaaac ttctacggcg gcggcctggg ttcggtgcgc    1980
ggatacgaaa gcggcacgct cggtccgaaa gtctatgacg aatacggcga aaaaatcagc    2040
tacggcggca acaaaaaagc caacgtctcc gccgagctgc tcttcccgat gcccggcgcg    2100
aaagacgcgc gcaccgtccg cctgagcctg tttgccgacg caggcagcgt gtgggacggc    2160
aaaacctacg acgacaacag cagttccgcg accggcggca gggttcaaaa catttacggc    2220
gccggcaata cccataaatc cacctttacc aacgaattgc gctattccgc cggcggcgcg    2280
gttacctggc tctcgccttt aggcccgatg aaattcagct acgcctaccc gctgaagaaa    2340
aaaccggaag acgaaatcca acgcttccaa ttccaactcg gcacgacgtt ctaa           2394
```

<210> SEQ ID NO 3
<211> LENGTH: 797
<212> TYPE: PRT
<213> ORGANISM: Neisseria meningitidis

<400> SEQUENCE: 3

```
Met Lys Leu Lys Gln Ile Ala Ser Ala Leu Met Met Leu Gly Ile Ser
 1               5                  10                  15

Pro Leu Ala Leu Ala Asp Phe Thr Ile Gln Asp Ile Arg Val Glu Gly
                20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
        50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
            100                 105                 110

Leu Glu Ser Phe Gly Leu Ala Gln Ser Gln Tyr Phe Asn Gln Ala Thr
        115                 120                 125

Leu Asn Gln Ala Val Ala Gly Leu Lys Glu Glu Tyr Leu Gly Arg Gly
    130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
            180                 185                 190

Met Arg Gln Met Ser Leu Thr Glu Gly Gly Ile Trp Thr Trp Leu Thr
        195                 200                 205

Arg Ser Asn Gln Phe Asn Glu Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Lys Gln Thr Ile Lys
                245                 250                 255

Ile Thr Val His Glu Gly Gly Arg Phe Arg Trp Gly Lys Val Ser Ile
```

```
                260                 265                 270
Glu Gly Asp Thr Asn Glu Val Pro Lys Ala Glu Leu Glu Lys Leu Leu
            275                 280                 285

Thr Met Lys Pro Gly Lys Trp Tyr Glu Arg Gln Gln Met Thr Ala Val
        290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Glu Thr Lys Thr Val Asp
                325                 330                 335

Phe Val Leu His Ile Glu Pro Gly Arg Lys Ile Tyr Val Asn Glu Ile
            340                 345                 350

His Ile Thr Gly Asn Asn Lys Thr Arg Asp Glu Val Val Arg Arg Glu
        355                 360                 365

Leu Arg Gln Met Glu Ser Ala Pro Tyr Asp Thr Ser Lys Leu Gln Arg
370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
            420                 425                 430

Val Gln Asp Thr Gly Leu Val Met Ser Ala Gly Val Ser Gln Asp Asn
        435                 440                 445

Leu Phe Gly Thr Gly Lys Ser Ala Ala Leu Arg Ala Ser Arg Ser Lys
450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Val Tyr Gly Lys Ala Phe Asp Pro
                485                 490                 495

Arg Lys Ala Ser Thr Ser Ile Lys Gln Tyr Lys Thr Thr Thr Ala Gly
            500                 505                 510

Ala Gly Ile Arg Met Ser Val Pro Val Thr Glu Tyr Asp Arg Val Asn
        515                 520                 525

Phe Gly Leu Val Ala Glu His Leu Thr Val Asn Thr Tyr Asn Lys Ala
530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
        595                 600                 605

Tyr Ser Ala Thr His Asn Gln Thr Trp Phe Pro Leu Ser Lys Thr
610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Gly Asn Lys Lys Ala Asn
        675                 680                 685
```

```
Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ala Thr Gly Gly Arg Val Gln
            725                 730                 735

Asn Ile Tyr Gly Ala Gly Asn Thr His Lys Ser Thr Phe Thr Asn Glu
            740                 745                 750

Leu Arg Tyr Ser Ala Gly Gly Ala Val Thr Trp Leu Ser Pro Leu Gly
            755                 760                 765

Pro Met Lys Phe Ser Tyr Ala Tyr Pro Leu Lys Lys Pro Glu Asp
770                 775                 780

Glu Ile Gln Arg Phe Gln Phe Gln Leu Gly Thr Thr Phe
785                 790                 795

<210> SEQ ID NO 4
<211> LENGTH: 21
<212> TYPE: PRT
<213> ORGANISM: Neisseria meningitidis

<400> SEQUENCE: 4

Met Lys Leu Lys Gln Ile Ala Ser Ala Leu Met Met Leu Gly Ile Ser
1               5                   10                  15

Pro Leu Ala Leu Ala
            20

<210> SEQ ID NO 5
<211> LENGTH: 776
<212> TYPE: PRT
<213> ORGANISM: Neisseria meningitidis

<400> SEQUENCE: 5

Asp Phe Thr Ile Gln Asp Ile Arg Val Glu Gly Leu Gln Arg Thr Glu
1               5                   10                  15

Pro Ser Thr Val Phe Asn Tyr Leu Pro Val Lys Val Gly Asp Thr Tyr
                20                  25                  30

Asn Asp Thr His Gly Ser Ala Ile Ile Lys Ser Leu Tyr Ala Thr Gly
            35                  40                  45

Phe Phe Asp Asp Val Arg Val Glu Thr Ala Asp Gly Gln Leu Leu Leu
50                  55                  60

Thr Val Ile Glu Arg Pro Thr Ile Gly Ser Leu Asn Ile Thr Gly Ala
65                  70                  75                  80

Lys Met Leu Gln Asn Asp Ala Ile Lys Lys Asn Leu Glu Ser Phe Gly
                85                  90                  95

Leu Ala Gln Ser Gln Tyr Phe Asn Gln Ala Thr Leu Asn Gln Ala Val
            100                 105                 110

Ala Gly Leu Lys Glu Glu Tyr Leu Gly Arg Gly Lys Leu Asn Ile Gln
            115                 120                 125

Ile Thr Pro Lys Val Thr Lys Leu Ala Arg Asn Arg Val Asp Ile Asp
            130                 135                 140

Ile Thr Ile Asp Glu Gly Lys Ser Ala Lys Ile Thr Asp Ile Glu Phe
145                 150                 155                 160

Glu Gly Asn Gln Val Tyr Ser Asp Arg Lys Leu Met Arg Gln Met Ser
                165                 170                 175

Leu Thr Glu Gly Gly Ile Trp Thr Trp Leu Thr Arg Ser Asn Gln Phe
            180                 185                 190

Asn Glu Gln Lys Phe Ala Gln Asp Met Glu Lys Val Thr Asp Phe Tyr
```

```
            195                 200                 205
Gln Asn Asn Gly Tyr Phe Asp Phe Arg Ile Leu Asp Thr Asp Ile Gln
    210                 215                 220

Thr Asn Glu Asp Lys Thr Lys Gln Thr Ile Lys Ile Thr Val His Glu
225                 230                 235                 240

Gly Gly Arg Phe Arg Trp Gly Lys Val Ser Ile Glu Gly Asp Thr Asn
                245                 250                 255

Glu Val Pro Lys Ala Glu Leu Glu Lys Leu Leu Thr Met Lys Pro Gly
            260                 265                 270

Lys Trp Tyr Glu Arg Gln Gln Met Thr Ala Val Leu Gly Glu Ile Gln
        275                 280                 285

Asn Arg Met Gly Ser Ala Gly Tyr Ala Tyr Ser Glu Ile Ser Val Gln
    290                 295                 300

Pro Leu Pro Asn Ala Glu Thr Lys Thr Val Asp Phe Val Leu His Ile
305                 310                 315                 320

Glu Pro Gly Arg Lys Ile Tyr Val Asn Glu Ile His Ile Thr Gly Asn
                325                 330                 335

Asn Lys Thr Arg Asp Glu Val Val Arg Arg Glu Leu Arg Gln Met Glu
            340                 345                 350

Ser Ala Pro Tyr Asp Thr Ser Lys Leu Gln Arg Ser Lys Glu Arg Val
        355                 360                 365

Glu Leu Leu Gly Tyr Phe Asp Asn Val Gln Phe Asp Ala Val Pro Leu
    370                 375                 380

Ala Gly Thr Pro Asp Lys Val Asp Leu Asn Met Ser Leu Thr Glu Arg
385                 390                 395                 400

Ser Thr Gly Ser Leu Asp Leu Ser Ala Gly Trp Val Gln Asp Thr Gly
                405                 410                 415

Leu Val Met Ser Ala Gly Val Ser Gln Asp Asn Leu Phe Gly Thr Gly
            420                 425                 430

Lys Ser Ala Ala Leu Arg Ala Ser Arg Ser Lys Thr Thr Leu Asn Gly
        435                 440                 445

Ser Leu Ser Phe Thr Asp Pro Tyr Phe Thr Ala Asp Gly Val Ser Leu
    450                 455                 460

Gly Tyr Asp Val Tyr Gly Lys Ala Phe Asp Pro Arg Lys Ala Ser Thr
465                 470                 475                 480

Ser Ile Lys Gln Tyr Lys Thr Thr Thr Ala Gly Ala Gly Ile Arg Met
                485                 490                 495

Ser Val Pro Val Thr Glu Tyr Asp Arg Val Asn Phe Gly Leu Val Ala
            500                 505                 510

Glu His Leu Thr Val Asn Thr Tyr Asn Lys Ala Pro Lys His Tyr Ala
        515                 520                 525

Asp Phe Ile Lys Lys Tyr Gly Lys Thr Asp Gly Thr Asp Gly Ser Phe
    530                 535                 540

Lys Gly Trp Leu Tyr Lys Gly Thr Val Gly Trp Gly Arg Asn Lys Thr
545                 550                 555                 560

Asp Ser Ala Leu Trp Pro Thr Arg Gly Tyr Leu Thr Gly Val Asn Ala
                565                 570                 575

Glu Ile Ala Leu Pro Gly Ser Lys Leu Gln Tyr Tyr Ser Ala Thr His
            580                 585                 590

Asn Gln Thr Trp Phe Phe Pro Leu Ser Lys Thr Phe Thr Leu Met Leu
        595                 600                 605

Gly Gly Glu Val Gly Ile Ala Gly Gly Tyr Gly Arg Thr Lys Glu Ile
    610                 615                 620
```

```
Pro Phe Phe Glu Asn Phe Tyr Gly Gly Gly Leu Gly Ser Val Arg Gly
625                 630                 635                 640

Tyr Glu Ser Gly Thr Leu Gly Pro Lys Val Tyr Asp Glu Tyr Gly Glu
            645                 650                 655

Lys Ile Ser Tyr Gly Asn Lys Lys Ala Asn Val Ser Ala Glu Leu
        660                 665                 670

Leu Phe Pro Met Pro Gly Ala Lys Asp Ala Arg Thr Val Arg Leu Ser
        675                 680                 685

Leu Phe Ala Asp Ala Gly Ser Val Trp Asp Gly Lys Thr Tyr Asp Asp
        690                 695                 700

Asn Ser Ser Ser Ala Thr Gly Gly Arg Val Gln Asn Ile Tyr Gly Ala
705                 710                 715                 720

Gly Asn Thr His Lys Ser Thr Phe Thr Asn Glu Leu Arg Tyr Ser Ala
                725                 730                 735

Gly Gly Ala Val Thr Trp Leu Ser Pro Leu Gly Pro Met Lys Phe Ser
            740                 745                 750

Tyr Ala Tyr Pro Leu Lys Lys Lys Pro Glu Asp Glu Ile Gln Arg Phe
        755                 760                 765

Gln Phe Gln Leu Gly Thr Thr Phe
770                 775

<210> SEQ ID NO 6
<211> LENGTH: 2379
<212> TYPE: DNA
<213> ORGANISM: Neisseria gonorrhoeae

<400> SEQUENCE: 6
atgaaactga acagattgc ctccgcactg atgatgttgg gcatatcgcc tttggcattt    60
gccgacttca ccatccaaga catccgtgtc gaaggcttgc agcgtaccga gccgagcacc   120
gtattcaact acctgcccgt caaagtcggc gacacctaca cgacacaca cggcagtgcc   180 atcatcaaaa gcctgtacgc caccggtttc tttgacgacg tacgagtcga aactgcggac   240
gggcagcttc tgctgaccgt tatcgaacgc cccaccatcg gctcgctcaa catcaccggc   300
gccaaaatgc tgcaaaacga cgccatcaag aaaaaacctcg aatcgttcgg gctggcgcag   360
tcgcaatact ttaatcaggc gacactcaac caggcagtcg ccggcctgaa agaagaatac   420
ctcgggcgtg gcaaactcaa tatccaaatc acgcccaaag taaccaaact cgcccgcaac   480
cgcgtcgaca tcgacatcac gattgacgag ggcaaatccg ccaaaatcac gacatcgaa    540 tttgaaggca accaagtcta ttccgaccgc aaactgatgc ggcagatgtc gctgaccgaa   600
ggcggcattt ggacatggct gacacgaagc gaccggttcg accgccagaa attcgcccaa   660
gacatggaaa agtaaccga cttctaccag aacaacggct acttcgattt ccgtatcctc   720
gataccgaca tccaaaccaa cgaagacaaa accaggcaga ccatcaaaat caccgtccac   780
gaaggcggac gtttccgctg ggcaaagtg tcgattgaag cgacaccaa cgaagtcccc     840 aaggccgaac tggaaaaact gctgaccatg aagcccggca atggtacga acgccagcag   900 atgaccgccg tttggtgtga gattcagaac cgcatgggct cggcaggcta cgcatacagc   960
gaaatcagcg tacagccgct gccgaacgcc ggaaccaaaa ccgtcgattt cgtcctgcac  1020
atcgaaccgg ccggaaaat ctacgtcaac gaaatccaca tcaccggcaa caacaaaacc   1080
cgcgacgaag tcgtcgcccg cgaattgcgc caaatggaat ccgcgcctta cgacacctcc  1140
aagctgcaac gctccaaaga gcgcgtcgag cttttgggct acttcgacaa cgtacagttt  1200
gatgccgtcc cgcttgccgg tacgcccgac aaagtcgatt tgaacatgag cctgaccgaa  1260
```

-continued

```
cgctccaccg gctcgctcga cttgagcgcg ggctgggttc aggataccgg cttggtcatg    1320
tccgccggcg tatcgcagga caacctgttc ggtacgggca agtcggccgc cctgcgcgcc    1380
tcgcgaagca aaaccacgct caacggctcg ctgtcgttta ccgacccgta cttcacggca    1440
gacggggtca gcctgggcta cgatatttac ggaaaagcct tcgacccgcg caaagcatcg    1500
accagcgtca acaatataa aaccaccacc gccggcggcg gcgtaaggat gggtatcccc    1560
gttaccgaat cgaccgcgt caatttcggg ctggcggcgg aacacctgac cgtcaacacc    1620
tacaacaaag cacccaaacg ctatgccgac tttatcagga atacggcaa accgacggc     1680 gcagacggca gcttcaaagg cctgctgtac aaaggcaccg tcggctgggg cgcaacaag    1740 accgacagcg cgtcatggcc gacgcgcggc tacctgaccg gcgtaaatgc cgaaatcgcc    1800
ctgcccggca gcaaactgca atactactcc gccacccaca accaaacctg gttcttcccc    1860
ttaagcaaaa ccttcacgct gatgctcggc ggcgaagtcg gcattgcggg cggctacggc    1920
agaaccaaag aaatcccctt ctttgaaaac ttctacggcg gcggcctggg ttcggtgcgc    1980
ggctacgaaa gcggcacgct cggcccgaaa gtgtatgacg aatacggcga aaaatcagc     2040 tacggcggca caaaaaagc caacgtctcc gccgagctgc tcttcccgat gcccggtgcg    2100
aaagacgcac gcaccgtccg cctgagcctg tttgccgacg caggcagcgt gtgggacggc    2160
agaacctata ccgccgccga aaacggtaac aacaaatcgg tttactcgga aaacgcgcat    2220
aaatccacct ttaccaacga attgcgctat ccgccggcg gcgcggttac ctggctctcg    2280
cctttgggtc cgatgaaatt cagctacgcc taccgctga agaaaaaacc ggaagacgaa    2340
atccaacgct tccaattcca gctcggcacg acgttctaa                          2379
```

<210> SEQ ID NO 7
<211> LENGTH: 792
<212> TYPE: PRT
<213> ORGANISM: Neisseria gonorrhoeae

<400> SEQUENCE: 7

```
Met Lys Leu Lys Gln Ile Ala Ser Ala Leu Met Met Leu Gly Ile Ser
 1               5                  10                  15

Pro Leu Ala Phe Ala Asp Phe Thr Ile Gln Asp Ile Arg Val Glu Gly
                20                  25                  30

Leu Gln Arg Thr Glu Pro Ser Thr Val Phe Asn Tyr Leu Pro Val Lys
            35                  40                  45

Val Gly Asp Thr Tyr Asn Asp Thr His Gly Ser Ala Ile Ile Lys Ser
        50                  55                  60

Leu Tyr Ala Thr Gly Phe Phe Asp Asp Val Arg Val Glu Thr Ala Asp
 65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
                100                 105                 110

Leu Glu Ser Phe Gly Leu Ala Gln Ser Gln Tyr Phe Asn Gln Ala Thr
            115                 120                 125

Leu Asn Gln Ala Val Ala Gly Leu Lys Glu Glu Tyr Leu Gly Arg Gly
        130                 135                 140

Lys Leu Asn Ile Gln Ile Thr Pro Lys Val Thr Lys Leu Ala Arg Asn
145                 150                 155                 160

Arg Val Asp Ile Asp Ile Thr Ile Asp Glu Gly Lys Ser Ala Lys Ile
                165                 170                 175

Thr Asp Ile Glu Phe Glu Gly Asn Gln Val Tyr Ser Asp Arg Lys Leu
```

```
                      180                 185                 190
Met Arg Gln Met Ser Leu Thr Glu Gly Gly Ile Trp Thr Trp Leu Thr
                195                 200                 205

Arg Ser Asp Arg Phe Asp Arg Gln Lys Phe Ala Gln Asp Met Glu Lys
    210                 215                 220

Val Thr Asp Phe Tyr Gln Asn Asn Gly Tyr Phe Asp Phe Arg Ile Leu
225                 230                 235                 240

Asp Thr Asp Ile Gln Thr Asn Glu Asp Lys Thr Arg Gln Thr Ile Lys
                245                 250                 255

Ile Thr Val His Glu Gly Gly Arg Phe Arg Trp Gly Lys Val Ser Ile
                260                 265                 270

Glu Gly Asp Thr Asn Glu Val Pro Lys Ala Glu Leu Glu Lys Leu Leu
            275                 280                 285

Thr Met Lys Pro Gly Lys Trp Tyr Glu Arg Gln Gln Met Thr Ala Val
        290                 295                 300

Leu Gly Glu Ile Gln Asn Arg Met Gly Ser Ala Gly Tyr Ala Tyr Ser
305                 310                 315                 320

Glu Ile Ser Val Gln Pro Leu Pro Asn Ala Gly Thr Lys Thr Val Asp
                325                 330                 335

Phe Val Leu His Ile Glu Pro Gly Arg Lys Ile Tyr Val Asn Glu Ile
                340                 345                 350

His Ile Thr Gly Asn Asn Lys Thr Arg Asp Glu Val Val Arg Arg Glu
            355                 360                 365

Leu Arg Gln Met Glu Ser Ala Pro Tyr Asp Thr Ser Lys Leu Gln Arg
        370                 375                 380

Ser Lys Glu Arg Val Glu Leu Leu Gly Tyr Phe Asp Asn Val Gln Phe
385                 390                 395                 400

Asp Ala Val Pro Leu Ala Gly Thr Pro Asp Lys Val Asp Leu Asn Met
                405                 410                 415

Ser Leu Thr Glu Arg Ser Thr Gly Ser Leu Asp Leu Ser Ala Gly Trp
                420                 425                 430

Val Gln Asp Thr Gly Leu Val Met Ser Ala Gly Val Ser Gln Asp Asn
            435                 440                 445

Leu Phe Gly Thr Gly Lys Ser Ala Ala Leu Arg Ala Ser Arg Ser Lys
        450                 455                 460

Thr Thr Leu Asn Gly Ser Leu Ser Phe Thr Asp Pro Tyr Phe Thr Ala
465                 470                 475                 480

Asp Gly Val Ser Leu Gly Tyr Asp Ile Tyr Gly Lys Ala Phe Asp Pro
                485                 490                 495

Arg Lys Ala Ser Thr Ser Val Lys Gln Tyr Lys Thr Thr Ala Gly
            500                 505                 510

Gly Gly Val Arg Met Gly Ile Pro Val Thr Glu Tyr Asp Arg Val Asn
        515                 520                 525

Phe Gly Leu Ala Ala Glu His Leu Thr Val Asn Thr Tyr Asn Lys Ala
            530                 535                 540

Pro Lys Arg Tyr Ala Asp Phe Ile Arg Lys Tyr Gly Lys Thr Asp Gly
545                 550                 555                 560

Ala Asp Gly Ser Phe Lys Gly Leu Leu Tyr Lys Gly Thr Val Gly Trp
                565                 570                 575

Gly Arg Asn Lys Thr Asp Ser Ala Ser Trp Pro Thr Arg Gly Tyr Leu
            580                 585                 590

Thr Gly Val Asn Ala Glu Ile Ala Leu Pro Gly Ser Lys Leu Gln Tyr
        595                 600                 605
```

```
Tyr Ser Ala Thr His Asn Gln Thr Trp Phe Phe Pro Leu Ser Lys Thr
610                 615                 620

Phe Thr Leu Met Leu Gly Glu Val Gly Ile Ala Gly Gly Tyr Gly
625                 630                 635                 640

Arg Thr Lys Glu Ile Pro Phe Phe Glu Asn Phe Tyr Gly Gly Leu
                645                 650                 655

Gly Ser Val Arg Gly Tyr Glu Ser Gly Thr Leu Gly Pro Lys Val Tyr
                660                 665                 670

Asp Glu Tyr Gly Glu Lys Ile Ser Tyr Gly Gly Asn Lys Lys Ala Asn
                675                 680                 685

Val Ser Ala Glu Leu Leu Phe Pro Met Pro Gly Ala Lys Asp Ala Arg
                690                 695                 700

Thr Val Arg Leu Ser Leu Phe Ala Asp Ala Gly Ser Val Trp Asp Gly
705                 710                 715                 720

Arg Thr Tyr Thr Ala Ala Glu Asn Gly Asn Asn Lys Ser Val Tyr Ser
                725                 730                 735

Glu Asn Ala His Lys Ser Thr Phe Thr Asn Glu Leu Arg Tyr Ser Ala
                740                 745                 750

Gly Gly Ala Val Thr Trp Leu Ser Pro Leu Gly Pro Met Lys Phe Ser
                755                 760                 765

Tyr Ala Tyr Pro Leu Lys Lys Pro Glu Asp Glu Ile Gln Arg Phe
                770                 775                 780

Gln Phe Gln Leu Gly Thr Thr Phe
785                 790

<210> SEQ ID NO 8
<211> LENGTH: 21
<212> TYPE: PRT
<213> ORGANISM: Neisseria gonorrhoeae

<400> SEQUENCE: 8

Met Lys Leu Lys Gln Ile Ala Ser Ala Leu Met Met Leu Gly Ile Ser
1               5                   10                  15

Pro Leu Ala Phe Ala
            20

<210> SEQ ID NO 9
<211> LENGTH: 771
<212> TYPE: PRT
<213> ORGANISM: Neisseria gonorrhoeae

<400> SEQUENCE: 9

Asp Phe Thr Ile Gln Asp Ile Arg Val Glu Gly Leu Gln Arg Thr Glu
1               5                   10                  15

Pro Ser Thr Val Phe Asn Tyr Leu Pro Val Lys Val Gly Asp Thr Tyr
                20                  25                  30

Asn Asp Thr His Gly Ser Ala Ile Ile Lys Ser Leu Tyr Ala Thr Gly
            35                  40                  45

Phe Phe Asp Asp Val Arg Val Glu Thr Ala Asp Gly Gln Leu Leu Leu
        50                  55                  60

Thr Val Ile Glu Arg Pro Thr Ile Gly Ser Leu Asn Ile Thr Gly Ala
65                  70                  75                  80

Lys Met Leu Gln Asn Asp Ala Ile Lys Lys Asn Leu Glu Ser Phe Gly
                85                  90                  95

Leu Ala Gln Ser Gln Tyr Phe Asn Gln Ala Thr Leu Asn Gln Ala Val
                100                 105                 110

Ala Gly Leu Lys Glu Glu Tyr Leu Gly Arg Gly Lys Leu Asn Ile Gln
```

```
              115                 120                 125
Ile Thr Pro Lys Val Thr Lys Leu Ala Arg Asn Arg Val Asp Ile Asp
130                 135                 140
Ile Thr Ile Asp Glu Gly Lys Ser Ala Lys Ile Thr Asp Ile Glu Phe
145                 150                 155                 160
Glu Gly Asn Gln Val Tyr Ser Asp Arg Lys Leu Met Arg Gln Met Ser
                    165                 170                 175
Leu Thr Glu Gly Gly Ile Trp Thr Trp Leu Thr Arg Ser Asp Arg Phe
                180                 185                 190
Asp Arg Gln Lys Phe Ala Gln Asp Met Glu Lys Val Thr Asp Phe Tyr
                195                 200                 205
Gln Asn Asn Gly Tyr Phe Asp Phe Arg Ile Leu Asp Thr Asp Ile Gln
    210                 215                 220
Thr Asn Glu Asp Lys Thr Arg Gln Thr Ile Lys Ile Thr Val His Glu
225                 230                 235                 240
Gly Gly Arg Phe Arg Trp Gly Lys Val Ser Ile Glu Gly Asp Thr Asn
                    245                 250                 255
Glu Val Pro Lys Ala Glu Leu Glu Lys Leu Leu Thr Met Lys Pro Gly
                260                 265                 270
Lys Trp Tyr Glu Arg Gln Gln Met Thr Ala Val Leu Gly Glu Ile Gln
                275                 280                 285
Asn Arg Met Gly Ser Ala Gly Tyr Ala Tyr Ser Glu Ile Ser Val Gln
290                 295                 300
Pro Leu Pro Asn Ala Gly Thr Lys Thr Val Asp Phe Val Leu His Ile
305                 310                 315                 320
Glu Pro Gly Arg Lys Ile Tyr Val Asn Glu Ile His Ile Thr Gly Asn
                    325                 330                 335
Asn Lys Thr Arg Asp Glu Val Val Arg Arg Glu Leu Arg Gln Met Glu
                340                 345                 350
Ser Ala Pro Tyr Asp Thr Ser Lys Leu Gln Arg Ser Lys Glu Arg Val
                355                 360                 365
Glu Leu Leu Gly Tyr Phe Asp Asn Val Gln Phe Asp Ala Val Pro Leu
370                 375                 380
Ala Gly Thr Pro Asp Lys Val Asp Leu Asn Met Ser Leu Thr Glu Arg
385                 390                 395                 400
Ser Thr Gly Ser Leu Asp Leu Ser Ala Gly Trp Val Gln Asp Thr Gly
                    405                 410                 415
Leu Val Met Ser Ala Gly Val Ser Gln Asp Asn Leu Phe Gly Thr Gly
                420                 425                 430
Lys Ser Ala Ala Leu Arg Ala Ser Arg Ser Lys Thr Thr Leu Asn Gly
                435                 440                 445
Ser Leu Ser Phe Thr Asp Pro Tyr Phe Thr Ala Asp Gly Val Ser Leu
    450                 455                 460
Gly Tyr Asp Ile Tyr Gly Lys Ala Phe Asp Pro Arg Lys Ala Ser Thr
465                 470                 475                 480
Ser Val Lys Gln Tyr Lys Thr Thr Thr Ala Gly Gly Gly Val Arg Met
                    485                 490                 495
Gly Ile Pro Val Thr Glu Tyr Asp Arg Val Asn Phe Gly Leu Ala Ala
                500                 505                 510
Glu His Leu Thr Val Asn Thr Tyr Asn Lys Ala Pro Lys Arg Tyr Ala
                515                 520                 525
Asp Phe Ile Arg Lys Tyr Gly Lys Thr Asp Gly Ala Asp Gly Ser Phe
530                 535                 540
```

-continued

```
Lys Gly Leu Leu Tyr Lys Gly Thr Val Gly Trp Gly Arg Asn Lys Thr
545                 550                 555                 560

Asp Ser Ala Ser Trp Pro Thr Arg Gly Tyr Leu Thr Gly Val Asn Ala
            565                 570                 575

Glu Ile Ala Leu Pro Gly Ser Lys Leu Gln Tyr Tyr Ser Ala Thr His
        580                 585                 590

Asn Gln Thr Trp Phe Phe Pro Leu Ser Lys Thr Phe Thr Leu Met Leu
    595                 600                 605

Gly Gly Glu Val Gly Ile Ala Gly Gly Tyr Gly Arg Thr Lys Glu Ile
610                 615                 620

Pro Phe Phe Glu Asn Phe Tyr Gly Gly Leu Gly Ser Val Arg Gly
625                 630                 635                 640

Tyr Glu Ser Gly Thr Leu Gly Pro Lys Val Tyr Asp Glu Tyr Gly Glu
            645                 650                 655

Lys Ile Ser Tyr Gly Gly Asn Lys Lys Ala Asn Val Ser Ala Glu Leu
        660                 665                 670

Leu Phe Pro Met Pro Gly Ala Lys Asp Ala Arg Thr Val Arg Leu Ser
    675                 680                 685

Leu Phe Ala Asp Ala Gly Ser Val Trp Asp Gly Arg Thr Tyr Thr Ala
690                 695                 700

Ala Glu Asn Gly Asn Asn Lys Ser Val Tyr Ser Glu Asn Ala His Lys
705                 710                 715                 720

Ser Thr Phe Thr Asn Glu Leu Arg Tyr Ser Ala Gly Ala Val Thr
            725                 730                 735

Trp Leu Ser Pro Leu Gly Pro Met Lys Phe Ser Tyr Ala Tyr Pro Leu
        740                 745                 750

Lys Lys Lys Pro Glu Asp Glu Ile Gln Arg Phe Gln Phe Gln Leu Gly
    755                 760                 765

Thr Thr Phe
    770

<210> SEQ ID NO 10
<211> LENGTH: 2394
<212> TYPE: DNA
<213> ORGANISM: Neisseria meningitidis

<400> SEQUENCE: 10
atgaaactga aacagattgc ttccgcactg atggtcttgg catatcgcc tttggcactt        60 gccgacttca ccatccaaga catccgcgtc gaaggcttgc agcgtaccga gccgagtacc       120
gtattcaact acctgcccgt caaagtcggc gacacctaca cgacacaca cggcagtgcc       180 atcatcaaaa gcctgtacgc caccggtttc tttgacgacg tacgcgtcga aactgcggac       240
gggcagctcc tgctgaccgt tatcgaacgc cccaccatcg gctcgctcaa catcaccggc       300
gcaaaaatgc tgcaaaacga cgccattaag aaaaacctcg aatcgttcgg ctggcgcag       360 tcgcaatact ttaatcaggc gacactcaat caggcagtcg ccggcctgaa agaagaatac       420
ctcgggcgcg gcaaactcaa tatccaaatc acgcccaaag taccaaaact cgcccgcaac       480
cgcgtcgaca tcgacatcac gattgacgag ggcaaatccg ccaaaatcac cgacatcgaa       540
tttgaaggca accaagtcta ttccgaccgc aaactgatgc ggcagatgtc gctgaccgaa       600
ggcggcattt ggacatggct gacacgaagc aaccaattca cgagcagaa atttgcccaa       660 gacatggaaa agtaaccga cttctaccag aacaacggct acttcgattt ccgcatcctc       720
gataccgaca tccaaaccaa cgaagacaaa accaagcaga ccatcaaaat caccgtccac       780
gaaggcggac gtttccgttg ggcaaagtc tccatcgaag cgacaccaa cgaagtcccc       840
```

```
aaagccgaac tggaaaaact gctgaccatg aagcccggca atggtacga acgccagcag    900
atgaccgccg tttttgggtga gattcagaac cgcatgggct cggcaggcta cgcatacagc   960
gaaatcagcg tacagccgct gccaaacgcc gaaaccaaaa ccgtcgattt cgtcctgcac  1020
atcgaaccgg gccggaaaat ctacgtcaac gaaatccaca tcaccggcaa caacaaaacc  1080
cgcgacgaag tcgtgcgccg cgaattgcgc caaatggaat ccgcgcctta cgacacctcc  1140
aagctgcaac gctccaaaga gcgcgtcgag cttttgggct acttcgacaa cgtacagttt  1200
gatgccgtcc cgcttgccgg cacacccgac aaagtcgatt tgaacatgag cctgaccgaa  1260
cgttccaccg gctcgctcga cttgagcgcg ggctgggtac aggataccgg cctggtcatg  1320
tccgcaggcg tttcccaaga caacctgttc ggtacgggca gtcggccgc cctgcgcgcc  1380
tcacgaagca aaaccacgct caacggctcg ctgtcgttta ccgacccgta cttcacggca  1440
gacggggtca gcctgggcta cgatgtttac ggaaaagcct tcgacccgcg caaagcatcg  1500
accagcatca acaatataa aaccaccacg gcaggcgcag gcatccgcat gagcgtgcct  1560
gttaccgaat acgaccgcgt gaatttcggt ttggtggcag aacacctgac cgtcaacacc  1620
tacaacaaag cgcccaaaca ctatgccgac tttatcaaga aatacggcaa accgacggc  1680
acagacggca gcttcaaagg ctggctgtac aaaggtaccg tcggctgggg gcgcaacaaa  1740
accgacagcg cgttatggcc gacgcgcggc tacctgacgg gcgtgaacgc cgaaatcgcc  1800
ctgcccggca gcaaactgca atactactcc gccacccaca accaaacctg gttcttcccc  1860
ttaagcaaaa ccttcacgct gatgctcggc ggcgaagtcg gcattgcggg cggctacggc  1920
agaaccaaag aaatccccctt ctttgaaaac ttctacggcg gcggcctggg ttcggtgcgc  1980
ggatacgaaa gcggcacgct cggtccgaaa gtgtatgacg aatacggcga aaaatcagc  2040
tacggcggca caaaaaagc caacgtctcc gccgagctgc tcttcccgat gcccggcgcg  2100
aaagacgcgc gcaccgtccg cctgagcctg tttgccgacg caggcagcgt gtgggacggc  2160
aaaacctacg acgacaacag cagttccgcg accggcggca gggttcaaaa catttacggc  2220
gccggcaata cccataaatc caccttttacc aacgaattgc gctattccgc cggcggcgcg  2280
gttacctggc tctcgccttt aggcccgatg aaattcagct acgcctaccc gctgaagaaa  2340
aaaccggaag acgaaatcca acgcttccaa ttccaactcg gcacgacgtt ctaa        2394
```

<210> SEQ ID NO 11
<211> LENGTH: 797
<212> TYPE: PRT
<213> ORGANISM: Neisseria meningitidis

<400> SEQUENCE: 11

```
Met Lys Leu Lys Gln Ile Ala Ser Ala Leu Met Val Leu Gly Ile Ser
 1               5                  10                  15

Pro Leu Ala Leu Ala Asp Phe Thr Ile Gln Asp Ile Arg Val Glu Gly
            20                  25                  30

Leu Gln Arg Thr Glu Pro Ser Thr Val Phe Asn Tyr Leu Pro Val Lys
        35                  40                  45

Val Gly Asp Thr Tyr Asn Asp Thr His Gly Ser Ala Ile Ile Lys Ser
    50                  55                  60

Leu Tyr Ala Thr Gly Phe Phe Asp Asp Val Arg Val Glu Thr Ala Asp
65                  70                  75                  80

Gly Gln Leu Leu Leu Thr Val Ile Glu Arg Pro Thr Ile Gly Ser Leu
                85                  90                  95

Asn Ile Thr Gly Ala Lys Met Leu Gln Asn Asp Ala Ile Lys Lys Asn
```

-continued

```
                100                 105                 110
Leu Glu Ser Phe Gly Leu Ala Gln Ser Gln Tyr Phe Asn Gln Ala Thr
            115                 120                 125
Leu Asn Gln Ala Val Ala Gly Leu Lys Glu Glu Tyr Leu Gly Arg Gly
        130                 135                 140
Lys Leu Asn Ile Gln Ile Thr Pro Lys Val Thr Lys Leu Ala Arg Asn
145                 150                 155                 160
Arg Val Asp Ile Asp Ile Thr Ile Asp Glu Gly Lys Ser Ala Lys Ile
                165                 170                 175
Thr Asp Ile Glu Phe Glu Gly Asn Gln Val Tyr Ser Asp Arg Lys Leu
            180                 185                 190
Met Arg Gln Met Ser Leu Thr Glu Gly Gly Ile Trp Thr Trp Leu Thr
        195                 200                 205
Arg Ser Asn Gln Phe Asn Glu Gln Lys Phe Ala Gln Asp Met Glu Lys
    210                 215                 220
Val Thr Asp Phe Tyr Gln Asn Asn Gly Tyr Phe Asp Phe Arg Ile Leu
225                 230                 235                 240
Asp Thr Asp Ile Gln Thr Asn Glu Asp Lys Thr Lys Gln Thr Ile Lys
                245                 250                 255
Ile Thr Val His Glu Gly Gly Arg Phe Arg Trp Gly Lys Val Ser Ile
            260                 265                 270
Glu Gly Asp Thr Asn Glu Val Pro Lys Ala Glu Leu Glu Lys Leu Leu
        275                 280                 285
Thr Met Lys Pro Gly Lys Trp Tyr Glu Arg Gln Gln Met Thr Ala Val
    290                 295                 300
Leu Gly Glu Ile Gln Asn Arg Met Gly Ser Ala Gly Tyr Ala Tyr Ser
305                 310                 315                 320
Glu Ile Ser Val Gln Pro Leu Pro Asn Ala Glu Thr Lys Thr Val Asp
                325                 330                 335
Phe Val Leu His Ile Glu Pro Gly Arg Lys Ile Tyr Val Asn Glu Ile
            340                 345                 350
His Ile Thr Gly Asn Asn Lys Thr Arg Asp Glu Val Val Arg Arg Glu
        355                 360                 365
Leu Arg Gln Met Glu Ser Ala Pro Tyr Asp Thr Ser Lys Leu Gln Arg
    370                 375                 380
Ser Lys Glu Arg Val Glu Leu Leu Gly Tyr Phe Asp Asn Val Gln Phe
385                 390                 395                 400
Asp Ala Val Pro Leu Ala Gly Thr Pro Asp Lys Val Asp Leu Asn Met
                405                 410                 415
Ser Leu Thr Glu Arg Ser Thr Gly Ser Leu Asp Leu Ser Ala Gly Trp
            420                 425                 430
Val Gln Asp Thr Gly Leu Val Met Ser Ala Gly Val Ser Gln Asp Asn
        435                 440                 445
Leu Phe Gly Thr Gly Lys Ser Ala Ala Leu Arg Ala Ser Arg Ser Lys
    450                 455                 460
Thr Thr Leu Asn Gly Ser Leu Ser Phe Thr Asp Pro Tyr Phe Thr Ala
465                 470                 475                 480
Asp Gly Val Ser Leu Gly Tyr Asp Val Tyr Gly Lys Ala Phe Asp Pro
                485                 490                 495
Arg Lys Ala Ser Thr Ser Ile Lys Gln Tyr Lys Thr Thr Thr Ala Gly
            500                 505                 510
Ala Gly Ile Arg Met Ser Val Pro Val Thr Glu Tyr Asp Arg Val Asn
        515                 520                 525
```

```
Phe Gly Leu Val Ala Glu His Leu Thr Val Asn Thr Tyr Asn Lys Ala
            530                 535                 540

Pro Lys His Tyr Ala Asp Phe Ile Lys Lys Tyr Gly Lys Thr Asp Gly
545                 550                 555                 560

Thr Asp Gly Ser Phe Lys Gly Trp Leu Tyr Lys Gly Thr Val Gly Trp
                565                 570                 575

Gly Arg Asn Lys Thr Asp Ser Ala Leu Trp Pro Thr Arg Gly Tyr Leu
            580                 585                 590

Thr Gly Val Asn Ala Glu Ile Ala Leu Pro Gly Ser Lys Leu Gln Tyr
            595                 600                 605

Tyr Ser Ala Thr His Asn Gln Thr Trp Phe Phe Pro Leu Ser Lys Thr
        610                 615                 620

Phe Thr Leu Met Leu Gly Gly Glu Val Gly Ile Ala Gly Gly Tyr Gly
625                 630                 635                 640

Arg Thr Lys Glu Ile Pro Phe Phe Glu Asn Phe Tyr Gly Gly Gly Leu
                645                 650                 655

Gly Ser Val Arg Gly Tyr Glu Ser Gly Thr Leu Gly Pro Lys Val Tyr
            660                 665                 670

Asp Glu Tyr Gly Glu Lys Ile Ser Tyr Gly Asn Lys Lys Ala Asn
        675                 680                 685

Val Ser Ala Glu Leu Leu Phe Pro Met Pro Gly Ala Lys Asp Ala Arg
690                 695                 700

Thr Val Arg Leu Ser Leu Phe Ala Asp Ala Gly Ser Val Trp Asp Gly
705                 710                 715                 720

Lys Thr Tyr Asp Asp Asn Ser Ser Ala Thr Gly Gly Arg Val Gln
                725                 730                 735

Asn Ile Tyr Gly Ala Gly Asn Thr His Lys Ser Thr Phe Thr Asn Glu
                740                 745                 750

Leu Arg Tyr Ser Ala Gly Gly Ala Val Thr Trp Leu Ser Pro Leu Gly
            755                 760                 765

Pro Met Lys Phe Ser Tyr Ala Tyr Pro Leu Lys Lys Lys Pro Glu Asp
        770                 775                 780

Glu Ile Gln Arg Phe Gln Phe Gln Leu Gly Thr Thr Phe
785                 790                 795

<210> SEQ ID NO 12
<211> LENGTH: 21
<212> TYPE: PRT
<213> ORGANISM: Neisseria meningitidis

<400> SEQUENCE: 12

Met Lys Leu Lys Gln Ile Ala Ser Ala Leu Met Val Leu Gly Ile Ser
1               5                   10                  15

Pro Leu Ala Leu Ala
            20

<210> SEQ ID NO 13
<211> LENGTH: 776
<212> TYPE: PRT
<213> ORGANISM: Neisseria meningitidis

<400> SEQUENCE: 13

Asp Phe Thr Ile Gln Asp Ile Arg Val Glu Gly Leu Gln Arg Thr Glu
1               5                   10                  15

Pro Ser Thr Val Phe Asn Tyr Leu Pro Val Lys Val Gly Asp Thr Tyr
            20                  25                  30

Asn Asp Thr His Gly Ser Ala Ile Ile Lys Ser Leu Tyr Ala Thr Gly
```

```
                35                  40                  45
Phe Phe Asp Asp Val Arg Val Glu Thr Ala Asp Gly Gln Leu Leu Leu
50                  55                  60

Thr Val Ile Glu Arg Pro Thr Ile Gly Ser Leu Asn Ile Thr Gly Ala
65                  70                  75                  80

Lys Met Leu Gln Asn Asp Ala Ile Lys Lys Asn Leu Glu Ser Phe Gly
                85                  90                  95

Leu Ala Gln Ser Gln Tyr Phe Asn Gln Ala Thr Leu Asn Gln Ala Val
                100                 105                 110

Ala Gly Leu Lys Glu Glu Tyr Leu Gly Arg Gly Lys Leu Asn Ile Gln
                115                 120                 125

Ile Thr Pro Lys Val Thr Lys Leu Ala Arg Asn Arg Val Asp Ile Asp
        130                 135                 140

Ile Thr Ile Asp Glu Gly Lys Ser Ala Lys Ile Thr Asp Ile Glu Phe
145                 150                 155                 160

Glu Gly Asn Gln Val Tyr Ser Asp Arg Lys Leu Met Arg Gln Met Ser
                165                 170                 175

Leu Thr Glu Gly Gly Ile Trp Thr Trp Leu Thr Arg Ser Asn Gln Phe
                180                 185                 190

Asn Glu Gln Lys Phe Ala Gln Asp Met Glu Lys Val Thr Asp Phe Tyr
        195                 200                 205

Gln Asn Asn Gly Tyr Phe Asp Phe Arg Ile Leu Asp Thr Asp Ile Gln
        210                 215                 220

Thr Asn Glu Asp Lys Thr Lys Gln Thr Ile Lys Ile Thr Val His Glu
225                 230                 235                 240

Gly Gly Arg Phe Arg Trp Gly Lys Val Ser Ile Glu Gly Asp Thr Asn
                245                 250                 255

Glu Val Pro Lys Ala Glu Leu Glu Lys Leu Leu Thr Met Lys Pro Gly
                260                 265                 270

Lys Trp Tyr Glu Arg Gln Gln Met Thr Ala Val Leu Gly Glu Ile Gln
                275                 280                 285

Asn Arg Met Gly Ser Ala Gly Tyr Ala Tyr Ser Glu Ile Ser Val Gln
        290                 295                 300

Pro Leu Pro Asn Ala Glu Thr Lys Thr Val Asp Phe Val Leu His Ile
305                 310                 315                 320

Glu Pro Gly Arg Lys Ile Tyr Val Asn Glu Ile His Ile Thr Gly Asn
                325                 330                 335

Asn Lys Thr Arg Asp Glu Val Val Arg Arg Glu Leu Arg Gln Met Glu
                340                 345                 350

Ser Ala Pro Tyr Asp Thr Ser Lys Leu Gln Arg Ser Lys Glu Arg Val
                355                 360                 365

Glu Leu Leu Gly Tyr Phe Asp Asn Val Gln Phe Asp Ala Val Pro Leu
        370                 375                 380

Ala Gly Thr Pro Asp Lys Val Asp Leu Asn Met Ser Leu Thr Glu Arg
385                 390                 395                 400

Ser Thr Gly Ser Leu Asp Leu Ser Ala Gly Trp Val Gln Asp Thr Gly
                405                 410                 415

Leu Val Met Ser Ala Gly Val Ser Gln Asp Asn Leu Phe Gly Thr Gly
                420                 425                 430

Lys Ser Ala Ala Leu Arg Ala Ser Arg Ser Lys Thr Thr Leu Asn Gly
        435                 440                 445

Ser Leu Ser Phe Thr Asp Pro Tyr Phe Thr Ala Asp Gly Val Ser Leu
        450                 455                 460
```

-continued

Gly Tyr Asp Val Tyr Gly Lys Ala Phe Asp Pro Arg Lys Ala Ser Thr
465                 470                 475                 480

Ser Ile Lys Gln Tyr Lys Thr Thr Ala Gly Ala Gly Ile Arg Met
        485                 490                 495

Ser Val Pro Val Thr Glu Tyr Asp Arg Val Asn Phe Gly Leu Val Ala
            500                 505                 510

Glu His Leu Thr Val Asn Thr Tyr Asn Lys Ala Pro Lys His Tyr Ala
        515                 520                 525

Asp Phe Ile Lys Lys Tyr Gly Lys Thr Asp Gly Thr Asp Gly Ser Phe
        530                 535                 540

Lys Gly Trp Leu Tyr Lys Gly Thr Val Gly Trp Gly Arg Asn Lys Thr
545                 550                 555                 560

Asp Ser Ala Leu Trp Pro Thr Arg Gly Tyr Leu Thr Gly Val Asn Ala
                565                 570                 575

Glu Ile Ala Leu Pro Gly Ser Lys Leu Gln Tyr Tyr Ser Ala Thr His
            580                 585                 590

Asn Gln Thr Trp Phe Phe Pro Leu Ser Lys Thr Phe Thr Leu Met Leu
        595                 600                 605

Gly Gly Glu Val Gly Ile Ala Gly Gly Tyr Gly Arg Thr Lys Glu Ile
610                 615                 620

Pro Phe Phe Glu Asn Phe Tyr Gly Gly Leu Gly Ser Val Arg Gly
625                 630                 635                 640

Tyr Glu Ser Gly Thr Leu Gly Pro Lys Val Tyr Asp Glu Tyr Gly Glu
                645                 650                 655

Lys Ile Ser Tyr Gly Gly Asn Lys Lys Ala Asn Val Ser Ala Glu Leu
            660                 665                 670

Leu Phe Pro Met Pro Gly Ala Lys Asp Ala Arg Thr Val Arg Leu Ser
        675                 680                 685

Leu Phe Ala Asp Ala Gly Ser Val Trp Asp Gly Lys Thr Tyr Asp Asp
        690                 695                 700

Asn Ser Ser Ser Ala Thr Gly Gly Arg Val Gln Asn Ile Tyr Gly Ala
705                 710                 715                 720

Gly Asn Thr His Lys Ser Thr Phe Thr Asn Glu Leu Arg Tyr Ser Ala
                725                 730                 735

Gly Gly Ala Val Thr Trp Leu Ser Pro Leu Gly Pro Met Lys Phe Ser
            740                 745                 750

Tyr Ala Tyr Pro Leu Lys Lys Pro Glu Asp Glu Ile Gln Arg Phe
        755                 760                 765

Gln Phe Gln Leu Gly Thr Thr Phe
    770                 775

<210> SEQ ID NO 14
<211> LENGTH: 441
<212> TYPE: PRT
<213> ORGANISM: Neisseria meningitidis

<400> SEQUENCE: 14

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
 65                  70                  75                  80

Leu Gln Ser Phe Arg Leu Gly Cys Ala Asn Leu Lys Asn Arg Gln Gly
             85                  90                  95

Trp Gln Asp Val Cys Ala Gln Ala Phe Gln Thr Pro Val His Ser Phe
        100                 105                 110

Gln Ala Lys Gln Phe Phe Glu Arg Tyr Phe Thr Pro Trp Gln Val Ala
    115                 120                 125

Gly Asn Gly Ser Leu Ala Gly Thr Val Thr Gly Tyr Tyr Glu Pro Val
130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 15
<211> LENGTH: 579
<212> TYPE: PRT
<213> ORGANISM: Neisseria meningitidis

<400> SEQUENCE: 15

```
Cys Leu Gly Gly Gly Ser Phe Asp Leu Asp Ser Val Glu Thr Val
 1               5                  10                 15

Gln Asp Met His Ser Lys Pro Lys Tyr Glu Asp Glu Lys Ser Gln Pro
             20                  25                  30

Glu Ser Gln Gln Asp Val Ser Glu Asn Ser Gly Ala Ala Tyr Gly Phe
             35                  40                  45

Ala Val Lys Leu Pro Arg Arg Asn Ala His Phe Asn Pro Lys Tyr Lys
 50                  55                  60

Glu Lys His Lys Pro Leu Gly Ser Met Asp Trp Lys Lys Leu Gln Arg
 65                  70                  75                  80

Gly Glu Pro Asn Ser Phe Ser Glu Arg Asp Leu Glu Lys Lys Arg
             85                  90                  95

Gly Ser Ser Glu Leu Ile Glu Ser Lys Trp Glu Asp Gly Gln Ser Arg
            100                 105                 110

Val Val Gly Tyr Thr Asn Phe Thr Tyr Val Arg Ser Gly Tyr Val Tyr
            115                 120                 125

Leu Asn Lys Asn Asn Ile Asp Ile Lys Asn Asn Ile Val Leu Phe Gly
            130                 135                 140

Pro Asp Gly Tyr Leu Tyr Tyr Lys Gly Lys Glu Pro Ser Lys Glu Leu
145                 150                 155                 160

Pro Ser Glu Lys Ile Thr Tyr Lys Gly Thr Trp Asp Tyr Val Thr Asp
                165                 170                 175

Ala Met Glu Lys Gln Arg Phe Glu Gly Leu Gly Ser Ala Ala Gly Gly
            180                 185                 190

Asp Lys Ser Gly Ala Leu Ser Ala Leu Glu Glu Gly Val Leu Arg Asn
            195                 200                 205

Gln Ala Glu Ala Ser Ser Gly His Thr Asp Phe Gly Met Thr Ser Glu
210                 215                 220

Phe Glu Val Asp Phe Ser Asp Lys Thr Ile Lys Gly Thr Leu Tyr Arg
225                 230                 235                 240

Asn Asn Arg Ile Thr Gln Asn Asn Ser Glu Asn Lys Gln Ile Lys Thr
                245                 250                 255

Thr Arg Tyr Thr Ile Gln Ala Thr Leu His Gly Asn Arg Phe Lys Gly
                260                 265                 270

Lys Ala Leu Ala Ala Asp Lys Gly Ala Thr Asn Gly Ser His Pro Phe
            275                 280                 285

Ile Ser Asp Ser Asp Ser Leu Glu Gly Gly Phe Tyr Gly Pro Lys Gly
            290                 295                 300

Glu Glu Leu Ala Gly Lys Phe Leu Ser Asn Asn Lys Val Ala Ala
305                 310                 315                 320

Val Phe Gly Ala Lys Gln Lys Asp Lys Lys Asp Gly Glu Asn Ala Ala
                325                 330                 335

Gly Pro Ala Thr Glu Thr Val Ile Asp Ala Tyr Arg Ile Thr Gly Glu
            340                 345                 350

Glu Phe Lys Lys Glu Gln Ile Asp Ser Phe Gly Asp Val Lys Lys Leu
            355                 360                 365

Leu Val Asp Gly Val Glu Leu Ser Leu Leu Pro Ser Glu Gly Asn Lys
            370                 375                 380

Ala Ala Phe Gln His Glu Ile Glu Gln Asn Gly Val Lys Ala Thr Val
385                 390                 395                 400

Cys Cys Ser Asn Leu Asp Tyr Met Ser Phe Gly Lys Leu Ser Lys Glu
                405                 410                 415

Asn Lys Asp Asp Met Phe Leu Gln Gly Val Arg Thr Pro Val Ser Asp
            420                 425                 430
```

Val Ala Ala Arg Thr Glu Ala Asn Ala Lys Tyr Arg Gly Thr Trp Tyr
                435                 440                 445

Gly Tyr Ile Ala Asn Gly Thr Ser Trp Ser Gly Glu Ala Ser Asn Gln
    450                 455                 460

Glu Gly Gly Asn Arg Ala Glu Phe Asp Val Asp Phe Ser Thr Lys Lys
465                 470                 475                 480

Ile Ser Gly Thr Leu Thr Ala Lys Asp Arg Thr Ser Pro Ala Phe Thr
                485                 490                 495

Ile Thr Ala Met Ile Lys Asp Asn Gly Phe Ser Gly Val Ala Lys Thr
            500                 505                 510

Gly Glu Asn Gly Phe Ala Leu Asp Pro Gln Asn Thr Gly Asn Ser His
        515                 520                 525

Tyr Thr His Ile Glu Ala Thr Val Ser Gly Gly Phe Tyr Gly Lys Asn
    530                 535                 540

Ala Ile Glu Met Gly Gly Ser Phe Ser Phe Pro Gly Asn Ala Pro Glu
545                 550                 555                 560

Gly Lys Gln Glu Lys Ala Ser Val Val Phe Gly Ala Lys Arg Gln Gln
                565                 570                 575

Leu Val Gln

<210> SEQ ID NO 16
<211> LENGTH: 1401
<212> TYPE: PRT
<213> ORGANISM: Neisseria meningitidis

<400> SEQUENCE: 16

Pro Gln Ala Trp Ala Gly His Thr Tyr Phe Gly Ile Asn Tyr Gln Tyr
1               5                   10                  15

Tyr Arg Asp Phe Ala Glu Asn Lys Gly Lys Phe Ala Val Gly Ala Lys
                20                  25                  30

Asp Ile Glu Val Tyr Asn Lys Lys Gly Glu Leu Val Gly Lys Ser Met
            35                  40                  45

Thr Lys Ala Pro Met Ile Asp Phe Ser Val Val Ser Arg Asn Gly Val
    50                  55                  60

Ala Ala Leu Val Gly Asp Gln Tyr Ile Val Ser Val Ala His Asn Gly
65                  70                  75                  80

Gly Tyr Asn Asn Val Asp Phe Gly Ala Glu Gly Arg Asn Pro Asp Gln
                85                  90                  95

His Arg Phe Thr Tyr Lys Ile Val Lys Arg Asn Asn Tyr Lys Ala Gly
                100                 105                 110

Thr Lys Gly His Pro Tyr Gly Gly Asp Tyr His Met Pro Arg Leu His
            115                 120                 125

Lys Phe Val Thr Asp Ala Glu Pro Val Glu Met Thr Ser Tyr Met Asp
    130                 135                 140

Gly Arg Lys Tyr Ile Asp Gln Asn Asn Tyr Pro Asp Arg Val Arg Ile
145                 150                 155                 160

Gly Ala Gly Arg Gln Tyr Trp Arg Ser Asp Glu Asp Pro Asn Asn
                165                 170                 175

Arg Glu Ser Ser Tyr His Ile Ala Ser Ala Tyr Ser Trp Leu Val Gly
                180                 185                 190

Gly Asn Thr Phe Ala Gln Asn Gly Ser Gly Gly Thr Val Asn Leu
            195                 200                 205

Gly Ser Glu Lys Ile Lys His Ser Pro Tyr Gly Phe Leu Pro Thr Gly
    210                 215                 220

```
Gly Ser Phe Gly Asp Ser Gly Ser Pro Met Phe Ile Tyr Asp Ala Gln
225                 230                 235                 240

Lys Gln Lys Trp Leu Ile Asn Gly Val Leu Gln Thr Gly Asn Pro Tyr
            245                 250                 255

Ile Gly Lys Ser Asn Gly Phe Gln Leu Val Arg Lys Asp Trp Phe Tyr
                260                 265                 270

Glu Pro Arg Gln Asn Gly Lys Tyr Ser Phe Asn Asp Asn Gly Thr
        275                 280                 285

Gly Lys Ile Asn Ala Lys His Glu His Asn Ser Leu Pro Asn Arg Leu
            290                 295                 300

Lys Thr Arg Thr Val Gln Leu Phe Asn Val Ser Leu Ser Glu Thr Ala
305                 310                 315                 320

Arg Glu Pro Val Tyr His Ala Ala Gly Val Asn Ser Tyr Arg Pro
                325                 330                 335

Arg Leu Asn Asn Gly Glu Asn Ile Ser Phe Ile Asp Glu Gly Lys Gly
                340                 345                 350

Glu Leu Ile Leu Thr Ser Asn Ile Asn Gln Gly Ala Gly Gly Leu Tyr
                355                 360                 365

Phe Gln Gly Asp Phe Thr Val Ser Pro Glu Asn Asn Glu Thr Trp Gln
370                 375                 380

Gly Ala Gly Val His Ile Ser Glu Asp Ser Thr Val Thr Trp Lys Val
385                 390                 395                 400

Asn Gly Val Ala Asn Asp Arg Leu Ser Lys Ile Gly Lys Gly Thr Leu
                405                 410                 415

His Val Gln Ala Lys Gly Glu Asn Gln Gly Ser Ile Ser Val Gly Asp
                420                 425                 430

Gly Thr Val Ile Leu Asp Gln Gln Ala Asp Asp Lys Gly Lys Lys Gln
                435                 440                 445

Ala Phe Ser Glu Ile Gly Leu Val Ser Gly Arg Gly Thr Val Gln Leu
                450                 455                 460

Asn Ala Asp Asn Gln Phe Asn Pro Asp Lys Leu Tyr Phe Gly Phe Arg
465                 470                 475                 480

Gly Gly Arg Leu Asp Leu Asn Gly His Ser Leu Ser Phe His Arg Ile
                485                 490                 495

Gln Asn Thr Asp Glu Gly Ala Met Ile Val Asn His Asn Gln Asp Lys
                500                 505                 510

Glu Ser Thr Val Thr Ile Thr Gly Asn Lys Asp Ile Ala Thr Thr Gly
                515                 520                 525

Asn Asn Asn Ser Leu Asp Ser Lys Lys Glu Ile Ala Tyr Asn Gly Trp
530                 535                 540

Phe Gly Glu Lys Asp Thr Thr Lys Thr Asn Gly Arg Leu Asn Leu Val
545                 550                 555                 560

Tyr Gln Pro Ala Ala Glu Asp Arg Thr Leu Leu Leu Ser Gly Gly Thr
                565                 570                 575

Asn Leu Asn Gly Asn Ile Thr Gln Thr Asn Gly Lys Leu Phe Phe Ser
                580                 585                 590

Gly Arg Pro Thr Pro His Ala Tyr Asn His Leu Asn Asp His Trp Ser
                595                 600                 605

Gln Lys Glu Gly Ile Pro Arg Gly Glu Ile Val Trp Asp Asn Asp Trp
        610                 615                 620

Ile Asn Arg Thr Phe Lys Ala Glu Asn Phe Gln Ile Lys Gly Gly Gln
625                 630                 635                 640

Ala Val Val Ser Arg Asn Val Ala Lys Val Lys Gly Asp Trp His Leu
                645                 650                 655
```

```
Ser Asn His Ala Gln Ala Val Phe Gly Val Ala Pro His Gln Ser His
            660                 665                 670

Thr Ile Cys Thr Arg Ser Asp Trp Thr Gly Leu Thr Asn Cys Val Glu
        675                 680                 685

Lys Thr Ile Thr Asp Asp Lys Val Ile Ala Ser Leu Thr Lys Thr Asp
690                 695                 700

Ile Ser Gly Asn Val Asp Leu Ala Asp His Ala His Leu Asn Leu Thr
705                 710                 715                 720

Gly Leu Ala Thr Leu Asn Gly Ser Leu Ser Ala Asn Gly Asp Thr Arg
                725                 730                 735

Tyr Thr Val Ser His Tyr Ala Thr Gln Asn Gly Asn Leu Ser Leu Val
            740                 745                 750

Gly Asn Ala Gln Ala Thr Phe Asn Gln Ala Thr Leu Ser Gly Asn Thr
                755                 760                 765

Ser Ala Ser Gly Asn Ala Ser Phe Asn Leu Ser Asp His Ala Val Gln
770                 775                 780

Asn Gly Ser Leu Thr Leu Ser Gly Asn Ala Lys Ala Asn Val Ser His
785                 790                 795                 800

Ser Ala Leu Asn Gly Asn Val Ser Leu Ala Asp Lys Ala Val Phe His
                805                 810                 815

Phe Glu Ser Ser Arg Phe Thr Gly Gln Ile Ser Gly Gly Lys Asp Thr
                820                 825                 830

Ala Leu His Leu Lys Asp Ser Glu Trp Thr Leu Pro Ser Gly Thr Glu
            835                 840                 845

Leu Gly Asn Leu Asn Leu Asp Asn Ala Thr Ile Thr Leu Asn Ser Ala
            850                 855                 860

Tyr Arg His Asn Ala Ala Gly Ala Gln Thr Gly Ser Ala Thr Asp Ala
865                 870                 875                 880

Pro Arg Arg Arg Ser Arg Ser Arg Arg Ser Leu Leu Ser Val Thr
                885                 890                 895

Pro Pro Thr Ser Val Glu Ser Arg Phe Asn Thr Leu Thr Val Asn Gly
                900                 905                 910

Lys Leu Asn Gly Gln Gly Thr Phe Arg Phe Met Ser Glu Leu Phe Gly
            915                 920                 925

Tyr Arg Ser Asp Lys Leu Lys Leu Pro Glu Ser Ser Glu Gly Thr Tyr
            930                 935                 940

Thr Leu Ala Val Asn Asn Thr Gly Asn Glu Pro Ala Ser Leu Glu Gln
945                 950                 955                 960

Leu Thr Val Val Glu Gly Lys Asp Asn Lys Pro Leu Ser Glu Asn Leu
                965                 970                 975

Asn Phe Thr Leu Gln Asn Glu His Val Asp Ala Gly Ala Trp Arg Tyr
            980                 985                 990

Gln Leu Ile Arg Lys Asp Gly Glu Phe Arg Leu His Asn Pro Val Lys
            995                 1000                1005

Glu Gln Glu Leu Ser Asp Lys Leu Gly Lys Ala Glu Ala Lys Lys Gln
    1010                1015                1020

Ala Glu Lys Asp Asn Ala Gln Ser Leu Asp Ala Leu Ile Ala Ala Gly
1025                1030                1035                1040

Arg Asp Ala Val Glu Lys Thr Glu Ser Val Ala Glu Pro Ala Arg Gln
                1045                1050                1055

Ala Gly Gly Glu Asn Val Gly Ile Met Gln Ala Glu Glu Lys Lys
            1060                1065                1070

Arg Val Gln Ala Asp Lys Asp Thr Ala Leu Ala Lys Gln Arg Glu Ala
```

```
                1075                1080                1085
Glu Thr Arg Pro Ala Thr Thr Ala Phe Pro Arg Arg Val Leu Pro Gln
        1090                1095                1100

Leu Gln Pro Gln Pro Gln Pro Gln Arg Asp Leu Ile Ser Arg
1105                1110                1115                1120

Tyr Ala Asn Ser Gly Leu Ser Glu Phe Ser Ala Thr Leu Asn Ser Val
                1125                1130                1135

Phe Ala Val Gln Asp Glu Leu Asp Arg Val Phe Ala Glu Asp Arg Arg
        1140                1145                1150

Asn Ala Val Trp Thr Ser Gly Ile Arg Asp Thr Lys His Tyr Arg Ser
                1155                1160                1165

Gln Asp Phe Arg Ala Tyr Arg Gln Gln Thr Asp Leu Arg Gln Ile Gly
        1170                1175                1180

Met Gln Lys Asn Leu Gly Ser Gly Arg Val Gly Ile Leu Phe Ser His
1185                1190                1195                1200

Asn Arg Thr Glu Asn Thr Phe Asp Asp Gly Ile Gly Asn Ser Ala Arg
                1205                1210                1215

Leu Ala His Gly Ala Val Phe Gly Gln Tyr Gly Ile Asp Arg Phe Tyr
        1220                1225                1230

Ile Gly Ile Ser Ala Gly Ala Gly Phe Ser Ser Gly Ser Leu Ser Asp
        1235                1240                1245

Gly Ile Gly Gly Lys Ile Arg Arg Arg Val Leu His Tyr Gly Ile Gln
        1250                1255                1260

Ala Arg Tyr Arg Ala Gly Phe Gly Gly Phe Gly Ile Glu Pro His Ile
1265                1270                1275                1280

Gly Ala Thr Arg Tyr Phe Val Gln Lys Ala Asp Tyr Arg Tyr Glu Asn
                1285                1290                1295

Val Asn Ile Ala Thr Pro Gly Leu Ala Phe Asn Arg Tyr Arg Ala Gly
        1300                1305                1310

Ile Lys Ala Asp Tyr Ser Phe Lys Pro Ala Gln His Ile Ser Ile Thr
        1315                1320                1325

Pro Tyr Leu Ser Leu Ser Tyr Thr Asp Ala Ala Ser Gly Lys Val Arg
        1330                1335                1340

Thr Arg Val Asn Thr Ala Val Leu Ala Gln Asp Phe Gly Lys Thr Arg
1345                1350                1355                1360

Ser Ala Glu Trp Gly Val Asn Ala Glu Ile Lys Gly Phe Thr Leu Ser
                1365                1370                1375

Leu His Ala Ala Ala Lys Gly Pro Gln Leu Glu Ala Gln His Ser
        1380                1385                1390

Ala Gly Ile Lys Leu Gly Tyr Arg Trp
        1395                1400

<210> SEQ ID NO 17
<211> LENGTH: 591
<212> TYPE: PRT
<213> ORGANISM: Neisseria meningitidis

<400> SEQUENCE: 17

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
```

```
             50                  55                  60
Val Gln Arg Thr Val Ala Val Leu Ile Val Asn Ser Asp Lys Glu Gly
 65                  70                  75                  80

Thr Gly Glu Lys Glu Lys Val Glu Glu Asn Ser Asp Trp Ala Val Tyr
                 85                  90                  95

Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
                115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
                195                 200                 205

Lys Lys Arg Ala Ala Ser Val Lys Asp Val Leu Asn Ala Gly Trp Asn
210                 215                 220

Ile Lys Gly Val Lys Pro Gly Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
                260                 265                 270

Lys Ile Gly Ala Lys Thr Ser Val Ile Lys Glu Lys Asp Gly Lys Leu
                275                 280                 285

Val Thr Gly Lys Asp Lys Gly Glu Asn Gly Ser Ser Thr Asp Glu Gly
                290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Gln Gly Asn Ile
                355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
                435                 440                 445

Ser Val Ser Leu Gly Ala Gly Ala Asp Ala Pro Thr Leu Ser Val Asp
                450                 455                 460

Gly Asp Ala Leu Asn Val Gly Ser Lys Lys Asp Asn Lys Pro Val Arg
465                 470                 475                 480
```

```
Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
        515                 520                 525

Gly Leu Val Gln Ala Tyr Leu Pro Gly Lys Ser Met Met Ala Ile Gly
    530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
                580                 585                 590

<210> SEQ ID NO 18
<211> LENGTH: 608
<212> TYPE: PRT
<213> ORGANISM: Neisseria meningitidis

<400> SEQUENCE: 18

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
            20                  25                  30

Ile Arg Gln Val Leu Asp Arg Gln His Phe Glu Pro Asp Gly Lys Tyr
        35                  40                  45

His Leu Phe Gly Ser Arg Gly Glu Leu Ala Glu Arg Ser Gly His Ile
    50                  55                  60

Gly Leu Gly Lys Ile Gln Ser His Gln Leu Gly Asn Leu Met Ile Gln
65                  70                  75                  80

Gln Ala Ala Ile Lys Gly Asn Ile Gly Tyr Ile Val Arg Phe Ser Asp
                85                  90                  95

His Gly His Glu Val His Ser Pro Phe Asp Asn His Ala Ser His Ser
            100                 105                 110

Asp Ser Asp Glu Ala Gly Ser Pro Val Asp Gly Phe Ser Leu Tyr Arg
        115                 120                 125

Ile His Trp Asp Gly Tyr Glu His His Pro Ala Asp Gly Tyr Asp Gly
    130                 135                 140

Pro Gln Gly Gly Gly Tyr Pro Ala Pro Lys Gly Ala Arg Asp Ile Tyr
145                 150                 155                 160

Ser Tyr Asp Ile Lys Gly Val Ala Gln Asn Ile Arg Leu Asn Leu Thr
                165                 170                 175

Asp Asn Arg Ser Thr Gly Gln Arg Leu Ala Asp Arg Phe His Asn Ala
            180                 185                 190

Gly Ser Met Leu Thr Gln Gly Val Gly Asp Gly Phe Lys Arg Ala Thr
        195                 200                 205

Arg Tyr Ser Pro Glu Leu Asp Arg Ser Gly Asn Ala Ala Glu Ala Phe
    210                 215                 220

Asn Gly Thr Ala Asp Ile Val Lys Asn Ile Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Gly Asn Lys Met
            260                 265                 270
```

```
Ala Arg Ile Asn Asp Leu Ala Asp Met Ala Gln Leu Lys Asp Tyr Ala
            275                 280                 285

Ala Ala Ala Ile Arg Asp Trp Ala Val Gln Asn Pro Asn Ala Ala Gln
        290                 295                 300

Gly Ile Glu Ala Val Ser Asn Ile Phe Met Ala Ala Ile Pro Ile Lys
305                 310                 315                 320

Gly Ile Gly Ala Val Arg Gly Lys Tyr Gly Leu Gly Gly Ile Thr Ala
                325                 330                 335

His Pro Ile Lys Arg Ser Gln Met Gly Ala Ile Ala Leu Pro Lys Gly
            340                 345                 350

Lys Ser Ala Val Ser Asp Asn Phe Ala Asp Ala Ala Tyr Ala Lys Tyr
        355                 360                 365

Pro Ser Pro Tyr His Ser Arg Asn Ile Arg Ser Asn Leu Glu Gln Arg
370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
                405                 410                 415

Phe Asp Gly Lys Gly Phe Pro Asn Phe Glu Lys His Val Lys Tyr Asp
            420                 425                 430

Thr Lys Leu Asp Ile Gln Glu Leu Ser Gly Gly Ile Pro Lys Ala
        435                 440                 445

Lys Pro Val Phe Asp Ala Lys Pro Arg Trp Glu Val Asp Arg Lys Leu
450                 455                 460

Asn Lys Leu Thr Thr Arg Glu Gln Val Lys Asn Val Gln Glu Ile
465                 470                 475                 480

Arg Asn Gly Asn Ile Asn Ser Asn Phe Ser Gln His Ala Gln Leu Glu
            485                 490                 495

Arg Glu Ile Asn Lys Leu Lys Ser Ala Asp Glu Ile Asn Phe Ala Asp
        500                 505                 510

Gly Met Gly Lys Phe Thr Asp Ser Met Asn Asp Lys Ala Phe Ser Arg
    515                 520                 525

Leu Val Lys Ser Val Lys Glu Asn Gly Phe Thr Asn Pro Val Val Glu
530                 535                 540

Tyr Val Glu Ile Asn Gly Lys Ala Tyr Ile Val Arg Gly Asn Asn Arg
545                 550                 555                 560

Val Phe Ala Ala Glu Tyr Leu Gly Arg Ile His Glu Leu Lys Phe Lys
                565                 570                 575

Lys Val Asp Phe Pro Val Pro Asn Thr Ser Trp Lys Asn Pro Thr Asp
            580                 585                 590

Val Leu Asn Glu Ser Gly Asn Val Lys Arg Pro Arg Tyr Arg Ser Lys
        595                 600                 605

<210> SEQ ID NO 19
<211> LENGTH: 471
<212> TYPE: PRT
<213> ORGANISM: Neisseria meningitidis

<400> SEQUENCE: 19

Cys Gly Gly Gly Gly Gly Ser Pro Asp Val Lys Ser Ala Asp Thr
1               5                   10                  15

Leu Ser Lys Pro Ala Ala Pro Val Val Ser Glu Lys Glu Thr Glu Ala
            20                  25                  30

Lys Glu Asp Ala Pro Gln Ala Gly Ser Gln Gly Gln Gly Ala Pro Ser
        35                  40                  45
```

```
Ala Gln Gly Ser Gln Asp Met Ala Val Ser Glu Glu Asn Thr Gly
     50                  55                  60

Asn Gly Gly Ala Val Thr Ala Asp Asn Pro Lys Asn Glu Asp Glu Val
65                  70                  75                  80

Ala Gln Asn Asp Met Pro Gln Asn Ala Ala Gly Thr Asp Ser Ser Thr
                 85                  90                  95

Pro Asn His Thr Pro Asp Pro Asn Met Leu Ala Gly Asn Met Glu Asn
             100                 105                 110

Gln Ala Thr Asp Ala Gly Glu Ser Ser Gln Pro Ala Asn Gln Pro Asp
         115                 120                 125

Met Ala Asn Ala Ala Asp Gly Met Gln Gly Asp Pro Ser Ala Gly
    130                 135                 140

Gly Gln Asn Ala Gly Asn Thr Ala Ala Gln Gly Ala Asn Gln Ala Gly
145                 150                 155                 160

Asn Asn Gln Ala Ala Gly Ser Ser Asp Pro Ile Pro Ala Ser Asn Pro
                 165                 170                 175

Ala Pro Ala Asn Gly Gly Ser Asn Phe Gly Arg Val Asp Leu Ala Asn
             180                 185                 190

Gly Val Leu Ile Asp Gly Pro Ser Gln Asn Ile Thr Leu Thr His Cys
         195                 200                 205

Lys Gly Asp Ser Cys Ser Gly Asn Asn Phe Leu Asp Glu Glu Val Gln
    210                 215                 220

Leu Lys Ser Glu Phe Glu Lys Leu Ser Asp Ala Asp Lys Ile Ser Asn
225                 230                 235                 240

Tyr Lys Lys Asp Gly Lys Asn Asp Lys Phe Val Gly Leu Val Ala Asp
                 245                 250                 255

Ser Val Gln Met Lys Gly Ile Asn Gln Tyr Ile Ile Phe Tyr Lys Pro
             260                 265                 270

Lys Pro Thr Ser Phe Ala Arg Phe Arg Arg Ser Ala Arg Ser Arg Arg
         275                 280                 285

Ser Leu Pro Ala Glu Met Pro Leu Ile Pro Val Asn Gln Ala Asp Thr
    290                 295                 300

Leu Ile Val Asp Gly Glu Ala Val Ser Leu Thr Gly His Ser Gly Asn
305                 310                 315                 320

Ile Phe Ala Pro Glu Gly Asn Tyr Arg Tyr Leu Thr Tyr Gly Ala Glu
                 325                 330                 335

Lys Leu Pro Gly Gly Ser Tyr Ala Leu Arg Val Gln Gly Glu Pro Ala
             340                 345                 350

Lys Gly Glu Met Leu Ala Gly Ala Val Tyr Asn Gly Glu Val Leu
    355                 360                 365

His Phe His Thr Glu Asn Gly Arg Pro Tyr Pro Thr Arg Gly Arg Phe
    370                 375                 380

Ala Ala Lys Val Asp Phe Gly Ser Lys Ser Val Asp Gly Ile Ile Asp
385                 390                 395                 400

Ser Gly Asp Asp Leu His Met Gly Thr Gln Lys Phe Lys Ala Ala Ile
                 405                 410                 415

Asp Gly Asn Gly Phe Lys Gly Thr Trp Thr Glu Asn Gly Ser Gly Asp
             420                 425                 430

Val Ser Gly Lys Phe Tyr Gly Pro Ala Gly Glu Glu Val Ala Gly Lys
         435                 440                 445

Tyr Ser Tyr Arg Pro Thr Asp Ala Glu Lys Gly Gly Phe Gly Val Phe
    450                 455                 460

Ala Gly Lys Lys Glu Gln Asp
465                 470
```

<210> SEQ ID NO 20
<211> LENGTH: 255
<212> TYPE: PRT
<213> ORGANISM: Neisseria meningitidis

<400> SEQUENCE: 20

```
Cys Ser Ser Gly Gly Gly Val Ala Ala Asp Ile Gly Ala Gly Leu
 1               5                  10                  15

Ala Asp Ala Leu Thr Ala Pro Leu Asp His Lys Asp Lys Gly Leu Gln
                20                  25                  30

Ser Leu Thr Leu Asp Gln Ser Val Arg Lys Asn Glu Lys Leu Lys Leu
            35                  40                  45

Ala Ala Gln Gly Ala Glu Lys Thr Tyr Gly Asn Gly Asp Ser Leu Asn
        50                  55                  60

Thr Gly Lys Leu Lys Asn Asp Lys Val Ser Arg Phe Asp Phe Ile Arg
65                  70                  75                  80

Gln Ile Glu Val Asp Gly Gln Leu Ile Thr Leu Glu Ser Gly Glu Phe
                85                  90                  95

Gln Val Tyr Lys Gln Ser His Ser Ala Leu Thr Ala Phe Gln Thr Glu
            100                 105                 110

Gln Ile Gln Asp Ser Glu His Ser Gly Lys Met Val Ala Lys Arg Gln
        115                 120                 125

Phe Arg Ile Gly Asp Ile Ala Gly Glu His Thr Ser Phe Asp Lys Leu
130                 135                 140

Pro Glu Gly Gly Arg Ala Thr Tyr Arg Gly Thr Ala Phe Gly Ser Asp
145                 150                 155                 160

Asp Ala Gly Gly Lys Leu Thr Tyr Thr Ile Asp Phe Ala Ala Lys Gln
                165                 170                 175

Gly Asn Gly Lys Ile Glu His Leu Lys Ser Pro Glu Leu Asn Val Asp
            180                 185                 190

Leu Ala Ala Ala Asp Ile Lys Pro Asp Gly Lys Arg His Ala Val Ile
        195                 200                 205

Ser Gly Ser Val Leu Tyr Asn Gln Ala Glu Lys Gly Ser Tyr Ser Leu
    210                 215                 220

Gly Ile Phe Gly Gly Lys Ala Gln Glu Val Ala Gly Ser Ala Glu Val
225                 230                 235                 240

Lys Thr Val Asn Gly Ile Arg His Ile Gly Leu Ala Ala Lys Gln
                245                 250                 255
```

<210> SEQ ID NO 21
<211> LENGTH: 421
<212> TYPE: PRT
<213> ORGANISM: Neisseria meningitidis

<400> SEQUENCE: 21

```
Cys Gln Ser Lys Ser Ile Gln Thr Phe Pro Gln Pro Asp Thr Ser Val
 1               5                  10                  15

Ile Asn Gly Pro Asp Arg Pro Val Gly Ile Pro Asp Pro Ala Gly Thr
                20                  25                  30

Thr Val Gly Gly Gly Gly Ala Val Tyr Thr Val Pro His Leu Ser
            35                  40                  45

Leu Pro His Trp Ala Ala Gln Asp Phe Ala Lys Ser Leu Gln Ser Phe
        50                  55                  60

Arg Leu Gly Cys Ala Asn Leu Lys Asn Arg Gln Gly Trp Gln Asp Val
65                  70                  75                  80
```

Cys Ala Gln Ala Phe Gln Thr Pro Val His Ser Phe Gln Ala Lys Gln
                85                  90                  95

Phe Phe Glu Arg Tyr Phe Thr Pro Trp Gln Val Ala Gly Asn Gly Ser
            100                 105                 110

Leu Ala Gly Thr Val Thr Gly Tyr Tyr Glu Pro Val Leu Lys Gly Asp
        115                 120                 125

Asp Arg Arg Thr Ala Gln Ala Arg Phe Pro Ile Tyr Gly Ile Pro Asp
    130                 135                 140

Asp Phe Ile Ser Val Pro Leu Pro Ala Gly Leu Arg Ser Gly Lys Ala
145                 150                 155                 160

Leu Val Arg Ile Arg Gln Thr Gly Lys Asn Ser Gly Thr Ile Asp Asn
                165                 170                 175

Thr Gly Gly Thr His Thr Ala Asp Leu Ser Arg Phe Pro Ile Thr Ala
            180                 185                 190

Arg Thr Thr Ala Ile Lys Gly Arg Phe Glu Gly Ser Arg Phe Leu Pro
        195                 200                 205

Tyr His Thr Arg Asn Gln Ile Asn Gly Gly Ala Leu Asp Gly Lys Ala
    210                 215                 220

Pro Ile Leu Gly Tyr Ala Glu Asp Pro Val Glu Leu Phe Phe Met His
225                 230                 235                 240

Ile Gln Gly Ser Gly Arg Leu Lys Thr Pro Ser Gly Lys Tyr Ile Arg
                245                 250                 255

Ile Gly Tyr Ala Asp Lys Asn Glu His Pro Tyr Val Ser Ile Gly Arg
            260                 265                 270

Tyr Met Ala Asp Lys Gly Tyr Leu Lys Leu Gly Gln Thr Ser Met Gln
        275                 280                 285

Gly Ile Lys Ala Tyr Met Arg Gln Asn Pro Gln Arg Leu Ala Glu Val
    290                 295                 300

Leu Gly Gln Asn Pro Ser Tyr Ile Phe Phe Arg Glu Leu Ala Gly Ser
305                 310                 315                 320

Ser Asn Asp Gly Pro Val Gly Ala Leu Gly Thr Pro Leu Met Gly Glu
                325                 330                 335

Tyr Ala Gly Ala Val Asp Arg His Tyr Ile Thr Leu Gly Ala Pro Leu
            340                 345                 350

Phe Val Ala Thr Ala His Pro Val Thr Arg Lys Ala Leu Asn Arg Leu
        355                 360                 365

Ile Met Ala Gln Asp Thr Gly Ser Ala Ile Lys Gly Ala Val Arg Val
    370                 375                 380

Asp Tyr Phe Trp Gly Tyr Gly Asp Glu Ala Gly Glu Leu Ala Gly Lys
385                 390                 395                 400

Gln Lys Thr Thr Gly Tyr Val Trp Gln Leu Leu Pro Asn Gly Met Lys
                405                 410                 415

Pro Glu Tyr Arg Pro
            420

<210> SEQ ID NO 22
<211> LENGTH: 274
<212> TYPE: PRT
<213> ORGANISM: Neisseria meningitidis

<400> SEQUENCE: 22

Val Asn Arg Thr Ala Phe Cys Cys Leu Ser Leu Thr Thr Ala Leu Ile
1               5                   10                  15

Leu Thr Ala Cys Ser Ser Gly Gly Gly Val Ala Ala Asp Ile Gly
            20                  25                  30

-continued

```
Ala Gly Leu Ala Asp Ala Leu Thr Ala Pro Leu Asp His Lys Asp Lys
        35                  40                  45

Gly Leu Gln Ser Leu Thr Leu Asp Gln Ser Val Arg Lys Asn Glu Lys
        50                  55                  60

Leu Lys Leu Ala Ala Gln Gly Ala Glu Lys Thr Tyr Gly Asn Gly Asp
 65                  70                  75                  80

Ser Leu Asn Thr Gly Lys Leu Lys Asn Asp Lys Val Ser Arg Phe Asp
                85                  90                  95

Phe Ile Arg Gln Ile Glu Val Asp Gly Gln Leu Ile Thr Leu Glu Ser
               100                 105                 110

Gly Glu Phe Gln Val Tyr Lys Gln Ser His Ser Ala Leu Thr Ala Phe
               115                 120                 125

Gln Thr Glu Gln Ile Gln Asp Ser Glu His Ser Gly Lys Met Val Ala
               130                 135                 140

Lys Arg Gln Phe Arg Ile Gly Asp Ile Ala Gly Glu His Thr Ser Phe
145                 150                 155                 160

Asp Lys Leu Pro Glu Gly Gly Arg Ala Thr Tyr Arg Gly Thr Ala Phe
               165                 170                 175

Gly Ser Asp Asp Ala Gly Gly Lys Leu Thr Tyr Thr Ile Asp Phe Ala
               180                 185                 190

Ala Lys Gln Gly Asn Gly Lys Ile Glu His Leu Lys Ser Pro Glu Leu
               195                 200                 205

Asn Val Asp Leu Ala Ala Ala Asp Ile Lys Pro Asp Gly Lys Arg His
    210                 215                 220

Ala Val Ile Ser Gly Ser Val Leu Tyr Asn Gln Ala Glu Lys Gly Ser
225                 230                 235                 240

Tyr Ser Leu Gly Ile Phe Gly Gly Lys Ala Gln Glu Val Ala Gly Ser
               245                 250                 255

Ala Glu Val Lys Thr Val Asn Gly Ile Arg His Ile Gly Leu Ala Ala
               260                 265                 270

Lys Gln
```

OUTER MEMBRANE VESICLE (OMV) VACCINE COMPRISING N. MENINGITIDIS SEROGROUP B OUTER MEMBRANE PROTEINS

SUBMISSION OF SEQUENCE LISTING ON ASII TEXT FILE

The content of the following submission on ASCII text file is incorporated herein by reference in its entirety: a computer readable form (CRF) of the Sequence Listing (file name: 223002099700SubSeqList.txt, date recorded: Jul. 15, 2010, size: 90 KB).

All documents cited herein are hereby incorporated by reference in their entirety.

TECHNICAL FIELD

This invention relates to vaccines against *Neisseria meningitidis*, serogroup B (NmB).

BACKGROUND ART

*Neisseria meningitidis* is a non-motile, Gram-negative diplococcus human pathogen. It colonises the pharynx, causing meningitis and, occasionally, septicaemia in the absence of meningitis. In the United States the attack rate is 0.6-1 per 100,000 persons per year, and it can be much greater during outbreaks (see Lieberman et al. (1996) *JAMA* 275(19):1499-1503; Schuchat et al (1997) *N Engl J Med* 337(14):970-976). In developing countries, endemic disease rates are much higher and during epidemics incidence rates can reach 500 cases per 100,000 persons per year. Mortality is extremely high, at 10-20% in the United States, and much higher in developing countries. Following the introduction of the conjugate vaccine against *Haemophilus influenzae*, *N. meningitidis* is the major cause of bacterial meningitis at all ages in the United States (Schuchat et al (1997) supra).

Based on the organism's capsular polysaccharide, 12 serogroups of *N. meningitidis* have been identified. The meningococcal vaccine currently in use is a tetravalent polysaccharide vaccine composed of serogroups A, C, Y and W135. Following the success of the vaccination against *H. influenzae*, however, conjugate vaccines against serogroups A and C have been developed Serogroup B remains a problem, however, and it is currently responsible for approximately 50% of total meningitis in the United States, Europe, and South America. The polysaccharide approach cannot be used because the menB capsular polysaccharide is a polymer of a N-acetyl neuraminic acid that is also present in mammalian tissue. This results in tolerance to the antigen; indeed, if a response were elicited, it would be anti-self, and therefore undesirable. In order to avoid induction of autoimmunity and to induce a protective immune response, the capsular polysaccharide has, for instance, been chemically modified substituting the N-acetyl groups with N-propionyl groups, leaving the specific antigenicity unaltered (Romero & Outschoom (1994) *Clin Microbiol Rev* 7(4):559-575).

An efficacious outer-membrane vesicle (OMV) vaccine against serogroup B has been produced by the Norwegian National Institute of Public Health [e.g. Bjune et al. (1991) *Lancet* 338(8775):1093-96]. Whilst this vaccine is safe and prevents NmB disease, its efficacy is limited to the strain used to make the vaccine. Other vaccines based around outer-membrane preparations have also been reported. It is an object of the present invention to broaden the efficacy of these vaccines to other strains.

DISCLOSURE OF THE INVENTION

Surprisingly, it has been found that the addition of further defined components to OMV vaccines significantly broadens their efficacy.

Thus the present invention provides a composition comprising (a) a NmB outer membrane preparation, and (b) an immunogenic component selected from one or more of the following:
  a protein disclosed in WO99/57280, or an immunogenic fragment thereof;
  a protein disclosed in WO99/36544, or an immunogenic fragment thereof;
  a protein disclosed in WO99/24578, or an immunogenic fragment thereof;
  a protein disclosed in WO00/66791, or an immunogenic fragment thereof;
  a protein disclosed in Tettelin et al. [*Science* (2000) 287: 1809-1815], or an immunogenic fragment thereof;
  a protein disclosed in Parkhill et al. [*Nature* (2000) 404: 502-506], or an immunogenic fragment thereof;
  a protein disclosed in WO97/28273, or an immunogenic fragment thereof;
  a protein disclosed in WO96/29412, or an immunogenic fragment thereof;
  a protein disclosed in WO95/03413, or an immunogenic fragment thereof;
  a protein disclosed in WO99/31132, or an immunogenic fragment thereof;
  a protein disclosed in WO99/58683, or an immunogenic fragment thereof;
  a protein disclosed in WO99/55873, or an immunogenic fragment thereof; and/or
  *Neisseria meningitidis* protein PorA, TbpA, TbpB, PilC, OpA, or Omp85.

If the composition comprises a protein disclosed in WO99/24578, said protein preferably comprises an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, & 892, as disclosed in WO99/24578 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO99/36544, said protein preferably comprises an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76; 78, 80, 82, 84, 86, 88, & 90, as disclosed in WO99/36544 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in Tettelin et al. (i.e. a protein encoded by one of the genes disclosed therein), said protein preferably comprises an amino acid sequence selected from the group consisting of NMB0001 to NMB2160 (or a protein comprising an immunogenic fragment of one or more of these 2160 genes, or a protein comprising a sequence having sequence identity (preferably greater than 50% eg. 60%, 70%, 80%, 90%, 95%, 99% or more) to one of these 2160 genes).

If the composition comprises a protein disclosed in Parkhill et al., said protein preferably comprises an amino acid sequence selected from the group consisting of the 2121 coding sequences disclosed therein (or a protein comprising an immunogenic fragment of one or more of these 2121 sequences, or a protein comprising a sequence having sequence identity (preferably greater than 50% eg. 60%, 70%, 80%, 90%, 95%, 99% or more) to one of these 2121 sequences).

If the composition comprises a protein disclosed in WO99/57280, said protein preferably comprises an amino acid sequence selected from the group consisting of SEQ IDs 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 418, 420, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 498, 500, 502, 504, 506, 508, 510, 512, 514, 516, 518, 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, 812, 814, 816, 818, 820, 822, 824, 826, 828, 830, 832, 834, 836, 838, 840, 842, 844, 846, 848, 850, 852, 854, 856, 858, 860, 862, 864, 866, 868, 870, 872, 874, 876, 878, 880, 882, 884, 886, 888, 890, 892, 894, 896, 898, 900, 902, 904, 906, 908, 910, 912, 914, 916, 918, 920, 922, 924, 926, 928, 930, 932, 934, 936, 938, 940, 942, 944, 946, 948, 950, 952, 954, 956, 958, 960, 962, 964, 966, 968, 970, 972, 974, 976, 978, 980, 982, 984, 986, 988, 990, 992, 994, 996, 998, 1000, 1002, 1004, 1006, 1008, 1010, 1012, 1014, 1016, 1018, 1020, 1022, 1024, 1026, 1028, 1030, 1032, 1034, 1036, 1038, 1040, 1042, 1044, 1046, 1048, 1050, 1052, 1054, 1056, 1058, 1060, 1062, 1064, 1066, 1068, 1070, 1072, 1074, 1076, 1078, 1080, 1082, 1084, 1086, 1088, 1090, 1092, 1094, 1096, 1098, 1100, 1102, 1104, 1106, 1108, 1110, 1112, 1114, 1116, 1118, 1120, 1122, 1124, 1126, 1128, 1130, 1132, 1134, 1136, 1138, 1140, 1142, 1144, 1146, 1148, 1150, 1152, 1154, 1156, 1158, 1160, 1162, 1164, 1166, 1168, 1170, 1172, 1174, 1176, 1178, 1180, 1182, 1184, 1186, 1188, 1190, 1192, 1194, 1196, 1198, 1200, 1202, 1204, 1206, 1208, 1210, 1212, 1214, 1216, 1218, 1220, 1222, 1224, 1226, 1228, 1230, 1232, 1234, 1236, 1238, 1240, 1242, 1244, 1246, 1248, 1250, 1252, 1254, 1256, 1258, 1260, 1262, 1264, 1266, 1268, 1270, 1272, 1274, 1276, 1278, 1280, 1282, 1284, 1286, 1288, 1290, 1292, 1294, 1296, 1298, 1300, 1302, 1304, 1306, 1308, 1310, 1312, 1314, 1316, 1318, 1320, 1322, 1324, 1326, 1328, 1330, 1332, 1334, 1336, 1338, 1340, 1342, 1344, 1346, 1348, 1350, 1352, 1354, 1356, 1358, 1360, 1362, 1364, 1366, 1368, 1370, 1372, 1374, 1376, 1378, 1380, 1382, 1384, 1386, 1388, 1390, 1392, 1394, 1396, 1398, 1400, 1402, 1404, 1406, 1408, 1410, 1412, 1414, 1416, 1418, 1420, 1422, 1424, 1426, 1428, 1430, 1432, 1434, 1436, 1438, 1440, 1442, 1444, 1446, 1448, 1450, 1452, 1454, 1456, 1458, 1460, 1462, 1464, 1466, 1468, 1470, 1472, 1474, 1476, 1478, 1480, 1482, 1484, 1486, 1488, 1490, 1492, 1494, 1496, 1498, 1500, 1502, 1504, 1506, 1508, 1510, 1512, 1514, 1516, 1518, 1520, 1522, 1524, 1526, 1528, 1530, 1532, 1534, 1536, 1538, 1540, 1542, 1544, 1546, 1548, 1550, 1552, 1554, 1556, 1558, 1560, 1562, 1564, 1566, 1568, 1570, 1572, 1574, 1576, 1578, 1580, 1582, 1584, 1586, 1588, 1590, 1592, 1594, 1596, 1598, 1600, 1602, 1604, 1606, 1608, 1610, 1612, 1614, 1616, 1618, 1620, 1622, 1624, 1626, 1628, 1630, 1632, 1634, 1636, 1638, 1640, 1642, 1644, 1646, 1648, 1650, 1652, 1654, 1656, 1658, 1660, 1662, 1664, 1666, 1668, 1670, 1672, 1674, 1676, 1678, 1680, 1682, 1684, 1686, 1688, 1690, 1692, 1694, 1696, 1698, 1700, 1702, 1704, 1706, 1708, 1710, 1712, 1714, 1716, 1718, 1720, 1722, 1724, 1726, 1728, 1730, 1732, 1734, 1736, 1738, 1740, 1742, 1744, 1746, 1748, 1750, 1752, 1754, 1756, 1758, 1760, 1762, 1764, 1766, 1768, 1770, 1772, 1774, 1776, 1778, 1780, 1782, 1784, 1786, 1788, 1790, 1792, 1794, 1796, 1798, 1800, 1802, 1804, 1806, 1808, 1810, 1812, 1814, 1816, 1818, 1820, 1822, 1824, 1826, 1828, 1830, 1832, 1834, 1836, 1838, 1840, 1842, 1844, 1846, 1848, 1850, 1852, 1854, 1856, 1858, 1860, 1862, 1864, 1866, 1868, 1870, 1872, 1874, 1876, 1878, 1880, 1882, 1884, 1886, 1888, 1890, 1892, 1894, 1896, 1898, 1900, 1902, 1904, 1906, 1908, 1910, 1912, 1914, 1916, 1918, 1920, 1922, 1924, 1926, 1928, 1930, 1932, 1934, 1936, 1938, 1940, 1942, 1944, 1946, 1948, 1950, 1952, 1954, 1956, 1958, 1960, 1962, 1964, 1966, 1968, 1970, 1972, 1974, 1976, 1978, 1980, 1982, 1984, 1986, 1988, 1990, 1992, 1994, 1996, 1998, 2000, 2002, 2004, 2006, 2008, 2010, 2012, 2014, 2016, 2018, 2020, 2022, 2024, 2026, 2028, 2030, 2032, 2034, 2036, 2038, 2040, 2042, 2044, 2046, 2048, 2050, 2052, 2054, 2056, 2058, 2060, 2062, 2064, 2066, 2068, 2070, 2072, 2074, 2076, 2078, 2080, 2082, 2084, 2086, 2088, 2090, 2092, 2094, 2096, 2098, 2100, 2102, 2104, 2106, 2108, 2110, 2112, 2114, 2116, 2118, 2120, 2122, 2124, 2126, 2128, 2130, 2132, 2134, 2136, 2138, 2140, 2142, 2144, 2146, 2148, 2150, 2152, 2154, 2156, 2158, 2160, 2162, 2164, 2166, 2168, 2170, 2172, 2174, 2176, 2178, 2180, 2182, 2184, 2186, 2188, 2190, 2192, 2194, 2196, 2198, 2200, 2202, 2204, 2206, 2208, 2210, 2212, 2214, 2216, 2218, 2220, 2222, 2224, 2226, 2228, 2230, 2232, 2234, 2236, 2238, 2240, 2242, 2244, 2246, 2248, 2250, 2252, 2254, 2256, 2258, 2260, 2262, 2264, 2266, 2268, 2270, 2272, 2274, 2276, 2278, 2280, 2282, 2284, 2286, 2288, 2290, 2292, 2294, 2296, 2298, 2300, 2302, 2304, 2306, 2308, 2310, 2312, 2314, 2316, 2318, 2320, 2322, 2324, 2326, 2328, 2330, 2332, 2334, 2336, 2338, 2340, 2342, 2344, 2346, 2348, 2350, 2352, 2354, 2356, 2358, 2360, 2362, 2364, 2366, 2368, 2370, 2372, 2374, 2376, 2378, 2380, 2382, 2384, 2386, 2388, 2390, 2392, 2394, 2396, 2398, 2400, 2402, 2404, 2406, 2408, 2410, 2412, 2414, 2416, 2418, 2420, 2422, 2424, 2426, 2428, 2430, 2432, 2434, 2436, 2438, 2440, 2442, 2444, 2446, 2448, 2450, 2452, 2454, 2456, 2458, 2460, 2462, 2464, 2466, 2468, 2470, 2472, 2474, 2476, 2478, 2480, 2482, 2484, 2486, 2488, 2490, 2492, 2494, 2496, 2498, 2500, 2502, 2504, 2506, 2508, 2510, 2512, 2514, 2516, 2518, 2520, 2522, 2524, 2526, 2528, 2530, 2532, 2534, 2536, 2538, 2540, 2542, 2544, 2546, 2548, 2550, 2552, 2554, 2556, 2558, 2560, 2562, 2564, 2566, 2568, 2570, 2572, 2574, 2576, 2578, 2580, 2582, 2584, 2586, 2588, 2590, 2592, 2594, 2596, 2598, 2600, 2602, 2604, 2606, 2608, 2610, 2612, 2614, 2616, 2618, 2620, 2622, 2624, 2626, 2628, 2630, 2632, 2634, 2636, 2638, 2640, 2642, 2644, 2646, 2648, 2650, 2652, 2654, 2656, 2658, 2660, 2662, 2664, 2666, 2668, 2670, 2672, 2674, 2676, 2678, 2680, 2682, 2684, 2686, 2688, 2690, 2692, 2694, 2696, 2698, 2700, 2702, 2704, 2706, 2708, 2710, 2712, 2714, 2716, 2718, 2720, 2722, 2724, 2726, 2728, 2730, 2732, 2734, 2736, 2738, 2740, 2742, 2744, 2746, 2748, 2750, 2752, 2754, 2756, 2758, 2760, 2762, 2764, 2766, 2768, 2770, 2772, 2774, 2776, 2778, 2780, 2782, 2784, 2786, 2788, 2790, 2792, 2794, 2796, 2798, 2800, 2802, 2804, 2806, 2808, 2810, 2812, 2814, 2816, 2818, 2820, 2822, 2824, 2826, 2828, 2830, 2832, 2834, 2836, 2838, 2840, 2842, 2844, 2846, 2848, 2850, 2852, 2854, 2856, 2858, 2860, 2862, 2864, 2866, 2868, 2870, 2872, 2874, 2876, 2878, 2880, 2882, 2884, 2886, 2888, 2890, 2892, 2894, 2896, 2898, 2900, 2902, 2904, 2906, 2908, 2910, 2912, 2914, 2916, 2918, 2920, 2922, 2924, 2926, 2928, 2930, 2932, 2934, 2936, 2938, 2940, 2942, 2944, 2946, 2948, 2950, 2952, 2954, 2956, 2958, 2960, 2962, 2964, 2966, 2968, 2970, 2972, 2974, 2976, 2978, 2980, 2982, 2984, 2986, 2988, 2990, 2992, 2994, 2996, 2998, 3000, 3002, 3004, 3006, 3008, 3010, 3012, 3014, 3016, 3018 & 3020, as disclosed in WO99/57280 (or a protein comprising an immunogenic fragment of one or more of these SEQ IDs, or a protein comprising a sequence having sequence identity (preferably greater than 50% e.g., 60%, 70%, 80%, 90%, 95%, 99% or more) to one of these SEQ IDs). The amino acid sequence of the mature form of m741.pep set forth as residues 20-274 of SEQ ID NO:2536 in WO99/57280 corresponds to SEQ ID NO:20 of the present application:

```
C SSGGGGVAAD IGAGLADALT APLDHKDKGL QSLTLDQSVR KNEKLKLAAQ GAEKTYGNGD

SLNTGKLKND KVSRFDFIRQ IEVDGQLITL ESGEFQVYKQ SHSALTAFQT EQIQDSEHSG

KMVAKRQFRI GDIAGEHTSF DKLPEGGRAT YRGTAFGSDD AGGKLTYTID FAAKQGNGKI

EHLKSPELNV DLAAADIKPD GKRHAVISGS VLYNQAEKGS YSLGIFGGKA QEVAGSAEVK

TVNGIRHIGL AAKQ.
```

If the composition comprises a protein disclosed in WO99/28273, said protein is preferably the protein disclosed in FIG. 4 or FIG. 13 of WO97/28273.

If the composition comprises a protein disclosed in WO96/29412, said protein preferably comprises an amino acid sequence selected from the group consisting of SEQ IDs 1-8 disclosed in WO96/29412 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO95/03413, said protein preferably comprises an amino acid sequence selected from the group consisting of SEQ IDs 1-23 disclosed in WO95/03413 (or a protein comprising an immunogenic fragment of one or more of these SEQ IDs, or a protein comprising a sequence having sequence identity (preferably greater than 50% eg. 60%, 70%, 80%, 90%, 95%, 99% or more) to one of these SEQ IDs).

If the composition comprises a protein disclosed in WO99/31132, said protein preferably comprises an amino acid sequence selected from the group consisting of SEQ ID 2 disclosed in WO99/31132 (or a protein comprising an immunogenic fragment of SEQ ID 2, or a protein comprising a sequence having sequence identity (preferably greater than 50% eg. 60%, 70%, 80%, 90%, 95%, 99% or more) to SEQ ID 2).

If the composition comprises a protein disclosed in WO99/58683, said protein preferably comprises an amino acid sequence selected from the group consisting of SEQ ID 2 or SEQ ID 4 disclosed in WO99/58683 (or a protein comprising an immunogenic fragment of SEQ ID 2 or SEQ ID 4, or a protein comprising a sequence having sequence identity (preferably greater than 50% eg. 60%, 70%, 80%, 90%, 95%, 99% or more) to SEQ ID 2 or SEQ ID 4).

If the composition comprises a protein disclosed in WO99/55873, said protein preferably comprises an amino acid sequence selected from the group consisting of SEQ ID 2 or SEQ ID 4 disclosed in WO99/55873 (or a protein comprising an immunogenic fragment of SEQ ID 2 or SEQ ID 4, or a protein comprising a sequence having sequence identity (preferably greater than 50% eg. 60%, 70%, 80%, 90%, 95%, 99% or more) to SEQ ID 2 or SEQ ID 4).

Details of Opa and PorA can be found in Wiertz et al. [Infect. Immun. (1996) 61: 298-304]. PilC is disclosed in Nassif et al. [PNAS USA (1994) 91: 3769-73]. Omp85 is disclosed in Manning et al. [Microb. Pathog. (1998) 25: 11-21]. TbpA and TbpB are disclosed in Ala'Aldeen & Borriello [Vaccine (1996) 14: 49-53] and also in Legrain et al. [Prorein Expr Purif (1995) δ: 570-578]. The amino acid sequence of the mature form of TbpB of Legrain et al. corresponds to SEQ ID NO:15 of the present application:

```
CLGGGGSFDL DSVETVQDMH SKPKYEDEKS QPESQQDVSE NSGAAYGFAV KLPRRNAHFN

PKYKEKHKPL GSMDWKKLQR GEPNSFSERD ELEKKRGSSE LIESKWEDGQ SRVVGYTNFT

YVRSGYVYLN KNNIDIKNNI VLFGPDGYLY YKGKEPSKEL PSEKITYKGT WDYVTDAMEK

QRFEGLGSAA GGDKSGALSA LEEGVLRNQA EASSGHTDFG MTSEFEVDFS DKTIKGTLYR

NNRITQNNSE NKQIKTTRYT IQATLHGNRF KGKALAADKG ATNGSHPFIS DSDSLEGGFY

GPKGEELAGK FLSNDNKVAA VFGAKQKDKK DGENAAGPAT ETVIDAYRIT GEEFKKEQID

SFGDVKKLLV DGVELSLLPS EGNKAAFQHE IEQNGVKATV CCSNLDYMSF GKLSKENKDD

MFLQGVRTPV SDVAARTEAN AKYRGTWYGY IANGTSWSGE ASNQEGGNRA EFDVDFSTKK

ISGTLTAKDR TSPAFTITAM IKDNGFSGVA KTGENGFALD PQNTGNSHYT HIEATVSGGF

YGKNAIEMGG SFSFPGNAPE GKQEKASVVF GAKRQQLVQ.
```

Preferred proteins for component (b) are:

protein '919', typified by SEQ IDs 3069-3074 and 3207-3241 of WO99/57280 (see also FIG. 23 and Example 15 therein). The amino acid sequence of the mature form of protein 919 set forth as residues 21-441 of SEQ ID NO:3070 in WO99/57280 corresponds to SEQ ID NO:21 of the present application:

```
CQSKSIQTFPQPDTSVINGPDRPVGIPDPAGTTVGGGGAVYTVVPHLSLPHWAAQDFAKSLQSFRLG

CANLKNRQGWQDVCAQAFQTPVHSFQAKQFFERYFTPWQVAGNGSLAGTVTGYYEPVLKGDDRRTAQ

ARFPIYGIPDDFISVPLPAGLRSGKALVRIRQTGKNSGTIDNTGGTHTADLSRFPITARTTAIKGRF

EGSRFLPYHTRNQINGGALDGKAPILGYAEDPVELFFMHIQGSGRLKTPSGKYIRIGYADKNEHPYV

SIGRYMADKGYLKLGQTSMQGIKAYMRQNPQRLAEVLGQNPSYIFFRELAGSSNDGPVGALGTPLMG

EYAGAVDRHYITLGAPLFVATAHPVTRKALNRLIMAQDTGSAIKGAVRVDYFWGYGDEAGELAGKQK

TTGYVWQLLPNGMKPEYRP.
``` protein '235', typified by SEQ IDs 869-874 and 3149-3178 of WO99/57280 (see also FIG. 1 and Example 12 therein).

protein '519', typified by SEQ IDs 3045-3056 and 3185-3206 of WO99/57280 (see also FIG. 22 and Example 14 therein).

protein '225', typified by SEQ IDs 793-804 and 3115-3148 of WO99/57280 (see also FIG. 19 and Example 11 therein).

protein 'ORF40', typified by example 1 (SEQ IDs 1-6) of WO99/36544 (see also FIG. 1 of WO00/66741; see also WO99/31132 and WO99/58683). The amino acid sequence of protein ORF40 set forth as SEQ ID NO:6 in WO99/36544 corresponds to SEQ ID NO:17 of the present application:

```
MNKIYRIIWN SALNAWVVVS ELTRNHTKRA SATVKTAVLA TLLFATVQAS ANNEEQEEDL

YLDPVQRTVA VLIVNSDKEG TGEKEKVEEN SDWAVYFNEK GVLTAREITL KAGDNLKIKQ

NGTNFTYSLK KDLTDLTSVG TEKLSFSANG NKVNITSDTK GLNFAKETAG TNGDTTVHLN

GIGSTLTDTL LNTGATTNVT NDNVTDDEKK RAASVKDVLN AGWNIKGVKP GTTASDNVDF

VRTYDTVEFL SADTKTTTVN VESKDNGKKT EVKIGAKTSV IKEKDGKLVT GKDKGENGSS

TDEGEGLVTA KEVIDAVNKA GWRMKTTTAN GQTGQADKFE TVTSGTNVTF ASGKGTTATV

SKDDQGNITV MYDVNVGDAL NVNQLQNSGW NLDSKAVAGS SGKVISGNVS PSKGKMDETV

NINAGNNIEI TRNGKNIDIA TSMTPQFSSV SLGAGADAPT LSVDGDALNV GSKKDNKPVR

ITNVAPGVKE GDVTNVAQLK GVAQNLNNRI DNVDGNARAG IAQAIATAGL VQAYLPGKSM

MAIGGGTYRG EAGYAIGYSS ISDGGNWIIK GTASGNSRGH FGASASVGYQ W*
``` protein '287', typified by example 9 of WO99/57280 (see SEQ IDs 1199-1204, 3103-3108 and 3179-3184 therein). The amino acid sequence of the mature form of protein 287 set forth as residues 18-488 of SEQ ID NO:1202 in WO99/57280 corresponds to SEQ ID NO:19 of the present application:

```
       CGG GGGGSPDVKS ADTLSKPAAP VVSEKETEAK EDAPQAGSQG QGAPSAQGSQ
DMAAVSEENT GNGGAVTADN PKNEDEVAQN DMPQNAAGTD SSTPNHTPDP NMLAGNMENQ
ATDAGESSQP ANQPDMANAA DGMQGDDPSA GGQNAGNTAA QGANQAGNNQ AAGSSDPIPA
SNPAPANGGS NFGRVDLANG VLIDGPSQNI TLTHCKGDSC SGNNFLDEEV QLKSEFEKLS
DADKISNYKK DGKNDKFVGL VADSVQMKGI NQYIIFYKPK PTSFARFRRS ARSRRSLPAE
MPLIPVNQAD TLIVDGEAVS LTGHSGNIFA PEGNYRYLTY GAEKLPGGSY ALRVQGEPAK
GEMLAGAAVY NGEVLHFHTE NGRPYPTRGR FAAKVDFGSK SVDGIIDSGD DLHMGTQKFK
AAIDGNGFKG TWTENGSGDV SGKFYGPAGE EVAGKYSYRP TDAEKGGFGV FAGKKEQD.
``` protein 'ORF1', typified by example 77 (SEQ IDs 647-654) of WO99/24578 (see also WO99/55873 and accession number AJ242535). The amino acid sequence of the mature form of protein ORF1 set forth as residues 48-1457 of SEQ ID NO:650 in WO99/24578 corresponds to SEQ ID NO:16 of the present application:

```
PQAWAGHTYFGINYQYYRDFAENKGKFAVGAKDIEVYNKKGELVGKSMTKAPMIDFSVVSRNGVAAL
VGDQYIVSVAHNGGYNNVDFGAEGRNPDQHRFTYKIVKRNNYKAGTKGHPYGGDYHMPRLHKFVTDA
EPVEMTSYMDGRKYIDQNNYPDRVRIGAGRQYWRSDEDEPNNRESSYHIASAYSWLVGGNTFAQNGS
GGGTVNLGSEKIKHSPYGFLPTGGSFGDSGSPMFIYDAQKQKWLINGVLQTGNPYIGKSNGFQLVRK
DWFYEPRQNGKYSFNDNNGTGKINAKHEHNSLPNRLKTRTVOLFNVSLSETAREPVYHAAGGVNSYR
PRLNNGENISFIDEGKGELILISNINQGAGGLYFQGDFTVSPENNETWQGAGVHISEDSTVTWKVNG
VANDRLSKIGKGTLHVOAKGENQGSISVGDGTVILDQQADDKGKKQAFSEIGLVSGRGTVOLNADNQ
FNPDKLYFGFRGGRLDLNGHSLSFHRIQNTDEGAMIVNHNQDKESTVTITGNKDIATTGNNNSLDSK
KEIAYNGWFGEKDTTKTNGRLNLVYQPAAEDRTLLLSGGTNLNGNITQTNGKLFFSGRPTPHAYNHL
NDHWSQKEGIPRGEIVWDNDWINRTFKAENFQIKGGQAVVSRNVAKVKGDWHLSNHAQAVFGVAPHQ
SHTICTRSDWTGLTNCVEKTITDDKVIASLTKTDISGNVDLADHAHLNLTGLATLNGSLSANGDTRY
TVSHYATQNGNLSLVGNAQATFNQATLSGNTSASGNASFNLSDHAVQNGSLTLSGNAKANVSHSALN
GNVSLADKAVFHFESSRFTGQISGGKDTALHLKDSEWTLPSGTELGNLNLDNATITLNSAYRHNAAG
AQTGSATDAPRRRSRRSRRSLLSVTPPTSVESRFNTLTVNGKLNGQGTFRFMSELFGYRSDKLKLPE
SSEGTYTLAVNNTGNEPASLEQLTVVEGKDNKPLSENLNFTLQNEHVDAGAWRYQLIRKDGEFRLHN
PVKEQELSDKLGKAEAKKQAEKDNAQSLDALIAAGRDAVEKTESVAEPARQAGGENVGIMQAEEEKK
RVQADKDTALAKQREAETRPATTAFPRRVLPQLQPQPQPQPQRDLISRYANSGLSEFSATLNSVFAV
QDELDRVFAEDRRNAVWTSGIRDTKHYRSQDFRAYRQQTDLRQIGMQKNLGSGRVGILFSHNRTENT
FDDGIGNSARLAHGAVFGQYGIDRFYIGISAGAGFSSGSLSDGIGGKIRRRVLHYGIQARYRAGFGG
FGIEPHIGATRYFVQKADYRYENVNIATPGLAFNRYRAGIKADYSFKPAQHISITPYLSLSYTDAAS
GKVRTRVNTAVLAQDFGKTRSAEWGVNAEIKGFTLSLHAAAAKGPQLEAQHSAGIKLGYRW.
``` protein 'ORF4', typified by example 26 (SEQ IDs 215-226) of WO99/24578 (see also FIG. 2 of WO00/66741).

protein 'ORF46', typified by example 55 (SEQ IDs 457-466) of WO99/24578 (see also FIG. 12 of WO00/66741). The amino acid sequence of the mature form of protein ORF46 of strain MC58 shown in FIG. 12 of WO00/66741 corresponds to SEQ ID NO:18 of the present application:

LGISRKISLILSILAVCLPMHAHASDLANDSFIRQVLDRQHFEPDGKYHLFGSRGELAERSGHI

GLGKIQSHQLGNLMIQQAAIKGNIGYIVRFSDHGHEVHSPFDNHASHSDSDEAGSPVDGFSLYR

IHWDGYEHHPADGYDGPQGGGYPAPKGARDIYSYDIKGVAQNIRLNLTDNRSTGQRLADRFHNA

GSMLTQGVGDGFKRATRYSPELDRSGNAAEAFNGTADIVKNIIGAAGEIVGAGDAVQGISEGSN

IAVMHGLGLLSTENKMARINDLADMAQLKDYAAAAIRDWAVQNPNAAQGIEAVSNIFMAAIPIK

GIGAVRGKYGLGGITAHPIKRSQMGAIALPKGKSAVSDNFADAAYAKYPSPYHSRNIRSNLEQR

YGKENITSSTVPPSNGKNVKLADQRHPKTGVPFDGKGFPNFEKHVKYDTKLDIQELSGGGIPKA

KPVFDAKPRWEVDRKLNKLTTREQVEKNVQEIRNGNINSNFSQHAQLEREINKLKSADEINFAD

GMGKFTDSMNDKAFSRLVKSVKENGFTNPVVEYVEINGKAYIVRGNNRVFAAEYLGRIHELKFK

KVDFPVPNTSWKNPTDVLNESGNVKRPRYRSK.

Component (b) of the composition is preferably a NmB protein. It is preferred that component (b) includes a protein from a different NmB strain from that from which the OMV of component (a) is derived i.e. the OMV in component (a) is preferably supplemented by immunogenic component (b) from a different NmB strain.

One or more of the components (or all of them) may be adsorbed on $Al(OH)_3$.

The Outer Membrane Preparation Component

The compositions of the invention include a NmB outer membrane preparation as component (a). This is preferably in the form of outer membrane vesicles (OMVs).

The preparation of OMVs from NmB is well-known in the art. Methods for obtaining suitable preparations are disclosed in, for instance: Claassen et al. [Vaccine (1996) 14:1001-1008]; Cartwright et al. [*Vaccine* (1999) 17:2612-2619]; Peeters et al. [*Vaccine* (1996) 14:1009-1015]; Fu et al. [*Biotechnology NY* (1995) 12:170-74]; Davies et al. [*J. Immunol. Meth.* (1990) 134:215-225]; Saunders et al. [*Infect. Immun.* (1999) 67:113-119]; Draabick et al. [*Vaccine* (2000) 18:160-172]; Moreno et al. [*Infect. Immun.* (1985) 47:527-533]; Milagres et al. [*Infect. Immun.* (1994) 62:4419-4424]; Naess et al. [*Infect. Immun.* (1998) 66:959-965]; Rosenqvist et al. [*Dev. Biol. Stand.* (1998) 92:323-333]; Haneberg et al. [*Infect. Immunn.* (1998) 66:1334-41]; Andersen et al. [*Vaccine* (1997) 15:1225-34]; Bjune et al. [*Lancet* (1991) 338:1093-96] etc.

OMVs are preferably a deoxycholate extract from NmB (i.e. obtained from NmB by deoxycholate extraction). The preferred extraction protocol is that described by Fredriksen et al. [Production, characterization and control of MenB-vaccine FOLKEHELSA™: an outer membrane vesicle vaccine against group B meningococcal disease (1991) NIPH Ann. 14(2):67-80].

A preferred strain from which to extract OMVs is the 44/76 strain (B:15:P1.7,16:P5.5:L3,7,9) of *N. meningitidis*.

Further details of the OMV component can be found in, for instance, Bjune et al. [Lancet (1991) 338(8775):1093-96], or Fredriksen et al. [Characterization of high molecular weight component in MenB-vaccine FOLKEHELSA™, an outer membrane vesicle vaccine against group B meningococcal disease. Pages 818-824 of Pathobiology and immunobiology of Neisseriaceae (eds. Conde-Glez et al.) ISBN. 968-6502-13-0].

The OMV component may be adsorbed to aluminium hydroxide adjuvant. A preferred protein:adjuvant ratio is 1:67 (wt/wt).

A typical dose of vaccine for a human contains 25 μg protein, 2 μg LPS and 1.67 mg $Al(OH)_3$, and can be injected in 0.5 ml volumes into the deltoid muscle.

The OMV component (e.g. as obtained by deoxycholate extraction) may be treated to remove certain components. For instance, pyrogens or toxic components may be removed (e.g. LPS).

It is preferred that the OMV component should retain the 80 kDa antigenic component described by Fredriksen et al. [pages 818-824 of *Pathobiology and immunobiology of Neisseriaceae*].

More preferably, the OMV component should retain a protein comprising one or more of the following amino acid sequences: SEQ ID 3, SEQ ID 5, SEQ ID 7, SEQ ID 9, SEQ ID 11, SEQ ID 13 [or (i) a protein having sequence identity to SEQ ID 3, SEQ ID 5, SEQ ID 7, SEQ ID 9, SEQ ID 11, or SEQ ID 13—depending on the particular SEQ ID, the degree of sequence identity is preferably greater than 50% (eg. 60%, 70%, 80%, 90%, 95%, 99% or more), which includes mutants and allelic variants, or (ii) a protein comprising an immunogenic fragment of SEQ ID 1, SEQ ID 3, SEQ ID 5, SEQ ID 7, SEQ ID 9, SEQ ID 11, or SEQ ID 13—the fragment should comprise at least n consecutive amino acids from the sequence and, depending on the particular sequence, n is 7 or more (eg. 8, 10, 12, 14, 16, 18, 20 or more).]

Combining Components (a) and (b)

Components (a) and (b) can be combined by simply mixing component (b) with an outer-membrane preparation (e.g. by mixing ORF4 with Norwegian OMVs).

As an alternative, they can be combined by manipulating a bacterium such that it produces (preferably hyperproduces) component (b) in its outer membrane—an outer-membrane preparation from such a recombinant bacterium will comprise both component (a) and component (b).

Suitable bacteria for manipulation in this way include *Neisseria meningitidis* (any serogroup or strain), *Neisseria lactamica, Neisseria cinerea* or any other non-typable *Neisseria*. Other Gram-negative bacteria can also be used, such as *E. coli, Salmonella, Shigella, Bordetella, Yersinia, Helicobacter*, etc. Transformation methods are well known in the art.

Multivalent Vaccines

Optionally, the composition of the invention may also comprise one or more of the following components:
- a protective antigen against *Neisseria meningitidis* serogroup A;
- a protective antigen against *Neisseria meningitidis* serogroup C;
- a protective antigen against *Neisseria meningitidis* serogroup Y;
- a protective antigen against *Neisseria meningitidis* serogroup W;
- a protective antigen against *Haemophilus influenzae*;
- a protective antigen against pneumococcus;
- a protective antigen against diphtheria;
- a protective antigen against tetanus;
- a protective antigen against whooping cough;
- a protective antigen against *Helicobacter pylori*;
- a protective antigen against polio; and/or
- a protective antigen against hepatitis B virus.

Preferred examples of these optional components are:
- a polysaccharide antigen against *Neisseria meningitidis* serogroup A;
- a polysaccharide antigen against *Neisseria meningitidis* serogroup C, such as that described in Costantino et al. (1992) *Vaccine* 10:691-698;
- a polysaccharide antigen against *Neisseria meningitidis* serogroup Y;
- a polysaccharide antigen against *Neisseria meningitidis* serogroup W;
- a polysaccharide antigen against *Haemophilus influenzae*;
- a polysaccharide antigen against pneumococcus;
- a protective antigen against diphtheria, consisting of a diphtheria toxoid, such as the CRM197 mutant [eg. Del Guidice et al., (1998) *Molecular Aspects of Medicine* 19:1-70].
- a protective antigen against tetanus, consisting of a tetanus toxoid [eg. Wassilak & Orenstein, Chapter 4 of Vaccines (eds. Plotkin & Mortimer), 1988]
- a protective antigen against whooping cough, comprising pertussis holotoxin (PT) and filamentous haemagglutinin (FHA); optionally further comprising pertactin and/or agglutinogens 2 and 3 [eg. Gustafsson et al. (1996) *N. Engl. J. Med.* 334:349-355; Rappuoli et al. (1991) *TIBTECH* 9:232-238].
- a protective antigen against *H. pylori*, comprising one or more of CagA (eg. WO93/18150), VacA (eg. WO93/18150), NAP (eg. WO99/53310), HopX (eg. WO98/04702), HopY (eg. WO98/04702), urease.
- a protective antigen against hepatitis B virus, consisting of a HBV surface antigen and/or a HBV core antigen.

Where the composition comprises an antigen against diphtheria, it preferably also comprises antigens against tetanus and polio. Where the composition comprises an antigen against tetanus, it preferably also comprises antigens against diphtheria and polio. Where the composition comprises an antigen against polio, it preferably also comprises antigens against diphtheria and tetanus.

Pertussis toxin is a toxic protein and, when present in the composition, it is preferably detoxified. Detoxification may be by chemical and/or genetic means. A preferred detoxified mutant is the 9K/129G double mutant [eg. Rappuoli (1997) *Nature Medicine* 3:374-376].

Where the composition includes a protein that exists in different nascent and mature forms, the mature form of the protein is preferably used. For example, where NspA is included, (WO96/29412; see also Martin et al. (1997) *J. Exp. Med.* 185 1173-1183) the mature form of the protein lacking the signal peptide is preferably used.

Where the composition includes a polysaccharide antigen, the polysaccharide is preferably conjugated to a carrier protein.

Therapy, Prophylaxis, Diagnosis

The composition of the invention is preferably a vaccine. Vaccines according to the invention may either be prophylactic (ie. to prevent infection) or therapeutic (ie. to treat disease after infection).

The invention also provides the compositions of the invention for use as medicaments (preferably as vaccines) or as diagnostic reagents. It also provides the use of a composition according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. Said Neisserial bacteria may be any species or strain (such as *N. gonorrhoeae*) but are preferably *N. meningitidis*, especially serogroup B (NmB).

The invention also provides a method of treating a patient, comprising administering to the patient a therapeutically effective amount of a composition according to the invention. The method is preferably immunisation.

Processes

According to further aspects, the invention provides various processes.

A process for producing a composition of the invention is provided, comprising the step of extraction (e.g. deoxycholate extraction) of OMVs from *N. meningitidis*.

Sequence Listing

The sequences in the sequence listing are:

| SEQ ID | DESCRIPTION |
| --- | --- |
| 1 | N-terminal sequence of *N. meningitidis* serogroup B protein, 80-85kDa |
| 2 | Complete gene from *N. meningitidis* serogroup B |
| 3 | Encoded protein from SEQ ID 2 |
| 4 | Signal peptide protein from SEQ ID 3 |
| 5 | Mature protein from SEQ ID 3 |
| 6 | Complete gene from *N. gonorrhoeae*, homologous to SEQ ID 2 |
| 7 | Encoded protein from SEQ ID 6 |
| 8 | Signal peptide protein from SEQ ID 7 |
| 9 | Mature protein from SEQ ID 7 |
| 10 | Complete gene from *N. meningitidis* serogroup A, homologous to SEQ ID 2 |
| 11 | Encoded protein from SEQ ID 10 |
| 12 | Signal peptide protein from SEQ ID 11 |
| 13 | Mature protein from SEQ ID 11 |
| 14 | Protein '919' from nmb strain 2996 |

MODES FOR CARRYING OUT THE INVENTION

A summary of standard techniques and procedures which may be employed in order to perform the invention (eg. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual*, Second Edition (1989); DNA Cloning, Volumes I and ii (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); *the Methods in Enzymology series* (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology*, Volumes I-IV (D. M. Weir and C. C. Blackwell eds 1986).

Standard abbreviations for nucleotides and amino acids are used in this specification.

Proteins used with the invention can be prepared by various means (eg. recombinant expression, purification from cell culture, chemical synthesis etc.) and in various forms (eg. native, fusions etc.). They are preferably prepared in substantially pure form (ie. substantially free from other *Neisseria* or host cell proteins).

Nucleic acid used with the invention can be prepared in many ways (eg. by chemical synthesis, from genomic or cDNA libraries; from the organism itself etc.) and can take various forms (eg. single stranded, double stranded, vectors, probes etc.). The term "nucleic acid" includes DNA and RNA, and also their analogues, such as those containing modified backbones, and also peptide nucleic acids (PNA) etc.

Definitions

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" eg. a composition "comprising" X may consist exclusively of X or may include something additional to X, such as X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

Identity between proteins is preferably determined by the Smith-Waterman homology search algorithm as implemented in the MPSRCH program (Oxford Molecular), using an affine gap search with parameters gap open penalty=12 and gap extension penalty=1. Typically, 50% identity or more between two proteins is considered to be an indication of functional equivalence.

As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (eg. see U.S. Pat. No. 5,753,235).

Expression Systems

The Neisserial nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (eg. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 by upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual*, 2nd ed.).

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter (Maniatis et al. (1987)

Science 236:1237; Alberts et al. (1989) *Molecular Biology of the Cell,* 2nd ed.]. Enhancer elements derived from viruses may be particularly useful, because they usually have a broader host range. Examples include the SV40 early gene enhancer [Dijkema et at (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual].*

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replicaton systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (eg. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene*, 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA*, 82:8404; mouse IL-3, (Miyajima et al., (1987) *Gene* 58:273; and human glucocerebrosidase, Martin et al. (1988) *DNA*, 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plagued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alfa: *Aedes aegypti, Autographa californica, Bombyx mori, Drosophila melanogaster, Spodoptera frugiperda*, and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg. Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, eg. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., *Nucleic Acids Research* 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillan, Gibberellins: in: *Advanced Plant Physiology.* Malcolm B. Wilkins, ed., 1984 Pitman Publishing Limited, London, pp. 21-52. References that describe other metabolically-regulated genes: Sheen, *Plant Cell,* 2:1027-1038 (1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in W ilmink and Dons, 1993, *Plant Mol. Biol. Reptr,* 11(2): 165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859-1863, 1982.

The vector may also be introduced into the plant cells by electroporation. (Fromm et al., *Proc. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Herocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding, site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al., (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann a al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz a al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences, derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al., (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbiol. Lett.* 60:273; Palva et al. (1982) *Proc. Natl. Acad. Sci. USA* 79:5582; EP-A-0 036 259 and EP-A-0 063953; WO 84/04541, *Bacillus*], [Miller et al. (1988) *Proc. Natl. Acad. Sci.* 85:856; Wang et al: (1990) *J. Bacteriol.* 172:949, *Campylobacter*], [Cohen et al. (1973) *Proc. Natl. Acad. Sci.* 69:2110; Dower a al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988). *Biochim. Biophys. Acta* 949:318; *Escherichia*], [Chassy a al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus* lactis by electroporation, in: *Streptococcal Genetics* (ed. J. Ferretti and R. Curtiss III);

Perry et al. (1981) *Infect. Immun.* 32:1295; Powell a al. (1988) *Appl. Environ. Microbiol.* 54:655; Somkuti et al. (1987) *Proc. 4th Evr. Cong. Biotechnology* 1:412, *Streptococcus].* v. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GA PDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: *Plasmids of Medical, Environmental and Commercial Importance* (eds. K. N. Timmis and A. Puhler); Mercerau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (eg. WO88/ 024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17-24], pCl/l [Brake a al. (1984) *Proc. Natl. Acad. Sci. USA* 81:4642- 4646], and YRp17 [Stinchcomb a al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2,11154, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 G aillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula]; [Das a al.* (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze a al. (1985) *J. Basic Microbiol.* 25:141; U.S. Pat. Nos. 4,837,148 and 4,929,555; Pichia]; [Hinnen a al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia]*.

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying Neisserial proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (eg. hypoxanthine, aminopterin, thymidine medium, "HAT").

The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in Vaccine design: the subunit and adjuvant approach, eds. Powell & Newman, Plenum Press 1995), containing 5% Squalene, 0.5% TWEEN 80™, and 0.5% SPAN 85™ (optionally containing various amounts of MTP PE (see below), although not required) formulated into submicron particles using a microfluidizer such as Model 110Y microfluidizer (Microfluidics, Newton, Mass.), (b) SAF, containing 10% Squalane, 0.4% TWEEN 80™, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% TWEEN 80™, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (eg. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection, either subcutaneously, intramuscularly, or transdermally/transcutaneously (eg. W 098/20734). Additional formulations suitable for other modes of administration include oral and pulmonary formulations, sup-positories, and transdermal applications. Dosage treatment may be a single dose schedule or a multiple dose schedule. The vaccine may be administered in conjunction with other immunoregulatory agents. As an alternative to protein-based vaccines, DNA vaccination may be employed [eg. Robinson & Torres (1997) *Seminars in Immunology* 9:271-283; Donnelly et al. (1997) *Annu Rev Immunol* 15:617-648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, lolly (1994) *Cancer Gene Therapy* 1:51-64; Kimura (1994) *Human Gene Therapy* 5:845-852; Connelly (1995) *Human Gene Therapy* 6:185-193; and Kaplitt (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses eg. MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a M urine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney M urine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, W 090/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, W 093/03769, WO93/19191, W 094/28938, WO95/11984, WO95/00655, W 095/27071, WO95/29993, W 095/34671, W 096/05320, WO94/08026, WO94/11506, WO93/06223, WO94/24299, WO95/14102, W 095/24297, W 095/02697, WO94/28152, W 094/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (ie. there is one sequence at each end) which are not involved in HP formation. The non-native replacement nucleotide may be any nucleotide other than the nucleotide found in the native D-sequence in the same position. Other employable exemplary AAV vectors are pW P-19, pW N-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, *Nature* 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569: 86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711.2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in USSN. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery, vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hem atopoetic, lymph cells, macrophages, dendritic cells, or tumor cells. Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins. etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Feigner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem.* 265:10189-10192), in functional form.

Cationic liposomes are readily available. For example, N(1-2,3-dioleyloxy)propyl]-N,N,N-triethylammonium (DOTMA) liposomes are available under the trademark Lipofectin, from GIBCO BRL, Grand Island, N.Y. (See, also, Feigner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *Proc. Natl. Acad. Sci. USA* 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow (1985) *Annu Rev. Biochem* 54:699; Law (1986) *Adv. Exp Med. Biol.* 151:162; Chen (1986) *J Biol Chem* 261:12918; Kane (1980) *Proc Natl Acad Sci USA* 77:2465; and Utermann (1984) *Hum Genet.* 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in Meth. Enzymol. 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Techniologies, Inc., Stoughton, Mass., USA. Further description of lipoproteins can be found in Zuckermann et al. WO 98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents. Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

Neisserial antigens of the invention can be used in immunoassays to detect antibody levels (or, conversely, anti-Neisserial antibodies can be used to detect antigen levels). Immunoassays based on well defined, recombinant antigens can be developed to replace invasive diagnostics methods. Antibodies to Neisserial proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immuno-precipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log_{10} Ci)+0.4[\% (G+C)]-0.6(\% \text{ formamide})-600/n-1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (ie. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Identification of the Meningococcal 80-85 kDa Protein

It was observed that various outer membrane vesicle preparations from *N. meningitidis* serogroup B contained a component of approximately 80-85 kDa. This protein was purified from SDS-PAGE gels and N-terminal sequenced (SEQ ID 1).

Antibodies raised against the SDS-PAGE purified protein cross-reacted with equivalent proteins in more than 50 *N. meningitidis* strains of diverse serogroups and serotypes. Cross-reactivity with *N. gonorrhoeae, N. polysaccharia* and *N. lactamica* was also observed. Post-immune sera from vaccinated patients also reacted with the protein.

The complete gene was cloned from serogroup B *N. meningitidis* (SEQ ID 2) and the encoded protein was inferred (SEQ ID 3). By comparison with the N-terminal sequencing described above, a signal peptide (SEQ ID 4) and a mature sequence (SEQ ID 5) are inferred.

Identification of Corresponding Genes in *N. meningitidis* serogroup A and *N. gonorrhoeae*

On the basis of the serogroup B *N. meningitidis* sequence, the corresponding genes from *N. meningitidis* serogroup A and *N. gonorrhoeae* were cloned and sequenced.

The complete gene from *N. gonorrhoeae* is shown in SEQ ID 6, with the encoded protein in SEQ ID 7. The signal peptide and mature sequence are SEQ IDs 8 and 9.

The complete gene from serogroup A *N. meningitidis* is shown in SEQ ID 10, with the encoded protein in SEQ ID 11. The signal peptide and mature sequence are SEQ IDs 12 and 13.

Sequence Comparisons

The protein sequences were compared and are highly homologous.

The *N. meningitidis* serogroup B sequence (orf21.pep; SEQ ID NO: 3) and the *N. gonorrhoeae* (orf21ng.pep; SEQ ID NO: 7) sequence show 95.4% identity in 797 aa overlap:

```
                        10        20        30        40        50        60
orf21.pep      MKLKQIASALMMLGISPLALADFTIQDIRVEGLQRTEPSTVFNYLPVKVGDTYNDTHGSA
               |||||||||||||||||||||:||||||||||||||||||||||||||||||||||||||
orf21ng.pep    MKLKQIASALMMLGISPLAFADFTIQDIRVEGLQRTEPSTVFNYLPVKVGDTYNDTHGSA
                        10        20        30        40        50        60

70        80        90       100       110       120
orf21.pep      IIKSLYATGFFDDVRVETADGQLLLTVIERPTIGSLNITGAKMLQNDAIKKNLESFGLAQ
               ||||||||||||||||||||||||||||||||||||||||||||||||||||||||||||
orf21ng.pep    IIKSLYATGFFDDVRVETADGQLLLTVIERPTIGSLNITGAKMLQNDAIKKNLESFGLAQ
                        70        80        90       100       110       120

130       140       150       160       170       180
orf21.pep      SQYFNQATLNQAVAGLKEEYLGRGKLNIQITPKVTKLARNRVDIDITIDEGKSAKITDIE
               ||||||||||||||||||||||||||||||||||||||||||||||||||||||||||||
orf21ng.pep    SQYFNQATLNQAVAGLKEEYLGRGKLNIQITPKVTKLARNRVDIDITIDEGKSAKITDIE
                       130       140       150       160       170       180

190       200       210       220       230       240
orf21.pep      FEGNQVYSDRKLMRQMSLTEGGIWTWLTRSNQFNEQKFAQDMEKVTDFYQNNGYFDFRIL
               ||||||||||||||||||||||||||||::|::|||||||||||||||||||||||||||
orf21ng.pep    FEGNQVYSDRKLMRQMSLTEGGIWTWLTRSDRFDRQKFAQDMEKVTDFYQNNGYFDFRIL
                       190       200       210       220       230       240

250       260       270       280       290       300
orf21.pep      DTDIQTNEDKTKQTIKITVHEGGRFRWGKVSIEGDTNEVPKAELEKLLTMKPGKWYERQQ
               |||||||||:||||||||||||||||||||||||||||||||||||||||||||||||||
orf21ng.pep    DTDIQTNEDKTRQTIKITVHEGGRFRWGKVSIEGDTNEVPKAELEKLLTMKPGKWYERQQ
                       250       260       270       280       290       300

310       320       330       340       350       360
orf21.pep      MTAVLGEIQNRMGSAGYAYSEISVQPLPNAETKTVDFVLHIEPGRKIYVNEIHITGNNKT
               ||||||||||||||||||||||||||||||||||||||||||||||||||||||||||||
orf21ng.pep    MTAVLGEIQNRMGSAGYAYSEISVQPLPNAGTKTVDFVLHIEPGRKIYVNEIHITGNNKT
                       310       320       330       340       350       360

370       380       390       400       410       420
orf21.pep      RDEVVRRELRQMESAPYDTSKLQRSKERVELLGYFDNVQFDAVPLAGTPDKVDLNMSLTE
               ||||||||||||||||||||||||||||||||||||||||||||||||||||||||||||
orf21ng.pep    RDEVVRRELRQMESAPYDTSKLQRSKERVELLGYFDNVQFDAVPLAGTPDKVDLNMSLTE
                       370       380       390       400       410       420

430       440       450       460       470       480
orf21.pep      RSTGSLDLSAGWVQDTGLVMSAGVSQDNLFGTGKSAALRASRSKTTLNGSLSFTDPYFTA
               ||||||||||||||||||||||||||||||||||||||||||||||||||||||||||||
orf21ng.pep    RSTGSLDLSAGWVQDTGLVMSAGVSQDNLFGTGKSAALRASRSKTTLNGSLSFTDPYFTA
                       430       440       450       460       470       480

490       500       510       520       530       540
orf21.pep      DGVSLGYDVYGKAFDPRKASTSIKQYKTTTAGAGIRMSVPVTEYDRVNFGLVAEHLTVNT
               ||||||||:||||||||||||||:|||||||||:|:||::|||||||||:|||||||||
orf21ng.pep    DGVSLGYDIYGKAFDPRKASTSVKQYKTTTAGGGVRMGIPVTEYDRVNFGLAAEHLTVNT
                       490       500       510       520       530       540
```

-continued

```
              550       560       570       580       590       600
orf21.pep     YNKAPKHYADFIKKYGKTDGTDGSFKGWLYKGTVGWGRNKTDSALWPTRGYLTGVNAEIA
              ||||||:||||| :||||||:||||||  |||||||||||||||| ||||||||||||||
orf21ng.pep   YNKAPKRYADFIRKYGKTDGADGSFKGLLYKGTVGWGRNKTDSASWPTRGYLTGVNAEIA
              550       560       570       580       590       600

610       620       630       640       650       660
orf21.pep     LPGSKLQYYSATHNQTWFFPLSKTFTLMLGGEVGIAGGYGRTKEIPFFENFYGGGLGSVR
              ||||||||||||||||||||||||||||||||||||||||||||||||||||||||||||
orf21ng.pep   LPGSKLQYYSATHNQTWFFPLSKTFTLMLGGEVGIAGGYGRTKEIPFFENFYGGGLGSVR
              610       620       630       640       650       660

670       680       690       700       710       720
orf21.pep     GYESGTLGPKVYDEYGEKISYGGNKKANVSAELLFPMPGAKDARTVRLSLFADAGSVWDG
              ||||||||||||||||||||||||||||||||||||||||||||||||||||||||||||
orf21ng.pep   GYESGTLGPKVYDEYGEKISYGGNKKANVSAELLFPMPGAKDARTVRLSLFADAGSVWDG
              670       680       690       700       710       720

730       740       750       760       770       780
orf21.pep     KTYDDNSSSATGGRVQNIYGAGNTHKSTFTNELRYSAGGAVTWLSPLGPMKFSYAYPLKK
              :||     ::  :|   :::|:  |:|||||||||||||||||||||||||||||||||
orf21ng.pep   RTY----TAAENGNNKSVYSE-NAHKSTFTNELRYSAGGAVTWLSPLGPMKFSYAYPLKK
                        730       740       750       760       770

790
orf21.pep     KPEDEIQRFQFQLGTTF    (SEQ ID NO: 3)
              |||||||||||||||||
orf21ng.pep   KPEDEIQRFQFQLGTTFX   (SEQ ID NO: 7)
              780       790
```

The N. meningitidis serogroup B (orf21.pep; SEQ ID NO: 3) and A (orf21a.pep; SEQ ID NO: 11) sequences show 99.9% identity in 797 aa overlap:

```
              10        20        30        40        50        60
orf21.pep     MKLKQIASALMMLGISPLALADFTIQDIRVEGLQRTEPSTVFNYLPVKVGDTYNDTHGSA
              |||||||||||:||||||||||||||||||||||||||||||||||||||||||||||||
orf21a.pep    MKLKQIASALMVLGISPLALADFTIQDIRVEGLQRTEPSTVFNYLPVKVGDTYNDTHGSA
              10        20        30        40        50        60

70        80        90        100       110       120
orf21.pep     IIKSLYATGFFDDVRVETADGQLLLTVIERPTIGSLNITGAKMLQNDAIKKNLESFGLAQ
              ||||||||||||||||||||||||||||||||||||||||||||||||||||||||||||
orf21a.pep    IIKSLYATGFFDDVRVETADGQLLLTVIERPTIGSLNITGAKMLQNDAIKKNLESFGLAQ
              70        80        90        100       110       120

130       140       150       160       170       180
orf21.pep     SQYFNQATLNQAVAGLKEEYLGRGKLNIQITPKVTKLARNRVDIDITIDEGKSAKITDIE
              ||||||||||||||||||||||||||||||||||||||||||||||||||||||||||||
orf21a.pep    SQYFNQATLNQAVAGLKEEYLGRGKLNIQITPKVTKLARNRVDIDITIDEGKSAKITDIE
              130       140       150       160       170       180

190       200       210       220       230       240
orf21.pep     FEGNQVYSDRKLMRQMSLTEGGIWTWLTRSNQFNEQKFAQDMEKVTDFYQNNGYFDFRIL
              ||||||||||||||||||||||||||||||||||||||||||||||||||||||||||||
orf21a.pep    FEGNQVYSDRKLMRQMSLTEGGIWTWLTRSNQFNEQKFAQDMEKVTDFYQNNGYFDFRIL
              190       200       210       220       230       240

250       260       270       280       290       300
orf21.pep     DTDIQTNEDKTKQTIKITVHEGGRFRWGKVSIEGDTNEVPKAELEKLLTMKPGKWYERQQ
              ||||||||||||||||||||||||||||||||||||||||||||||||||||||||||||
orf21a.pep    DTDIQTNEDKTKQTIKITVHEGGRFRWGKVSIEGDTNEVPKAELEKLLTMKPGKWYERQQ
              250       260       270       280       290       300

310       320       330       340       350       360
orf21.pep     MTAVLGEIQNRMGSAGYAYSEISVQPLPNAETKTVDFVLHIEPGRKIYVNEIHITGNNKT
              ||||||||||||||||||||||||||||||||||||||||||||||||||||||||||||
orf21a.pep    MTAVLGEIQNRMGSAGYAYSEISVQPLPNAETKTVDFVLHIEPGRKIYVNEIHITGNNKT
              310       320       330       340       350       360

370       380       390       400       410       420
orf21.pep     RDEVVRRELRQMESAPYDTSKLQRSKERVELLGYFDNVQFDAVPLAGTPDKVDLNMSLTE
              ||||||||||||||||||||||||||||||||||||||||||||||||||||||||||||
orf21a.pep    RDEVVRRELRQMESAPYDTSKLQRSKERVELLGYFDNVQFDAVPLAGTPDKVDLNMSLTE
              370       380       390       400       410       420

430       440       450       460       470       480
orf21.pep     RSTGSLDLSAGWVQDTGLVMSAGVSQDNLFGTGKSAALRASRSKTTLNGSLSFTDPYFTA
              ||||||||||||||||||||||||||||||||||||||||||||||||||||||||||||
orf21a.pep    RSTGSLDLSAGWVQDTGLVMSAGVSQDNLFGTGKSAALRASRSKTTLNGSLSFTDPYFTA
              430       440       450       460       470       480

490       500       510       520       530       540
orf21.pep     DGVSLGYDVYGKAFDPRKASTSIKQYKTTTAGAGIRMSVPVTEYDRVNFGLVAEHLTVNT
              ||||||||||||||||||||||||||||||||||||||||||||||||||||||||||||
orf21a.pep    DGVSLGYDVYGKAFDPRKASTSIKQYKTTTAGAGIRMSVPVTEYDRVNFGLVAEHLTVNT
              490       500       510       520       530       540
```

-continued

```
                550        560        570        580        590        600
orf21.pep    YNKAPKHYADFIKKYGKTDGTDGSFKGWLYKGTVGWGRNKTDSALWPTRGYLTGVNAEIA
             ||||||||||||||||||||||||||||||||||||||||||||||||||||||||||||
orf21a.pep   YNKAPKHYADFIKKYGKTDGTDGSFKGWLYKGTVGWGRNKTDSALWPTRGYLTGVNAEIA
                550        560        570        580        590        600

610        620        630        640        650        660
orf21.pep    LPGSKLQYYSATHNQTWFFPLSKTFTLMLGGEVGIAGGYGRTKEIPFFENFYGGGLGSVR
             ||||||||||||||||||||||||||||||||||||||||||||||||||||||||||||
orf21a.pep   LPGSKLQYYSATHNQTWFFPLSKTFTLMLGGEVGIAGGYGRTKEIPFFENFYGGGLGSVR
                610        620        630        640        650        660

670        680        690        700        710        720
orf21.pep    GYESGTLGPKVYDEYGEKISYGGNKKANVSAELLFPMPGAKDARTVRLSLFADAGSVWDG
             ||||||||||||||||||||||||||||||||||||||||||||||||||||||||||||
orf21a.pep   GYESGTLGPKVYDEYGEKISYGGNKKANVSAELLFPMPGAKDARTVRLSLFADAGSVWDG
                670        680        690        700        710        720

730        740        750        760        770        780
orf21.pep    KTYDDNSSSATGGRVQNIYGAGNTHKSTFTNELRYSAGGAVTWLSPLGPMKFSYAYPLKK
             ||||||||||||||||||||||||||||||||||||||||||||||||||||||||||||
orf21a.pep   KTYDDNSSSATGGRVQNIYGAGNTHKSTFTNELRYSAGGAVTWLSPLGPMKFSYAYPLKK
                730        740        750        760        770        780

790
orf21.pep    KPEDEIQRFQFQLGTTF   (SEQ ID 3)
             |||||||||||||||||
orf21a.pep   KPEDEIQRFQFQLGTTF   (SEQ ID 11)
                790
```

The high degree of conservation suggests that a single protein may be able to induce immune responses against a variety of Neisseriae species.

Vaccines

The three proteins identified above were expressed and used for immunisation. Good immune responses were observed against the proteins.

Combination Vaccines

In addition, the proteins were each combined with antigens against other pathogenic organisms (e.g. the Chiron polysaccharide vaccine against serogroup C meningitis), and used for immunisation. Good immune responses were observed.

Further NmB Components

Whilst it is efficacious, the protection elicited by the Norwegian OMV vaccine is restricted to the strain used to make the vaccine. The clinical trials on the vaccine obtained only 57.2% efficacy after 29 months in teenagers, although IgG responses were observed in almost 100% of patients [e.g. Rosenqvist et al. (1995) Infect. Immun. 63:4642-4652].

Surprisingly, it has been found that the addition of further defined components to the Norwegian OMV vaccine significantly broadens its efficacy.

The Norwegian vaccine does not elicit protection against NmB strain 2996. Defined proteins from strain 2996 were added to the Norwegian vaccine, and it was shown that the efficacy of the vaccine was increased by a surprising degree. Furthermore, the addition of a NmC polysaccharide conjugate antigen [e.g. Costantino et al. (1992) Vaccine 10:691-698] gave excellent results.

The bactericidal activities of the combinations are shown in the following table:

| Group | Norwegian OMV | NmB antigen* | NmC antigen | Bactericidal activity against NmB strain 2996 |
|---|---|---|---|---|
| 1 | + | — | — | <4 |
| 2 | + | #1 | — | 512 |
| 3 | + | #2 | — | >2048 |
| 4 | + | #3 | — | 1024 |
| 5 | + | #3 | + | 256 |
| 6 | — | #3 | — | 2048 |
| 7 | — | #3 | + | 2048 |

*Three different NmB antigens were used:
1: ORF1 -e.g. example 77 of WO99/24578 (see also WO99/55873)
2: protein '287' -e.g. FIG. 21 of WO99/57280 (also SEQ IDs 3103-3108)
3: a mixture in Al(OH)$_3$ of #1, #2 and protein '919' (SEQ ID 14 herein; see also WO99/57280 FIG. 23 and SEQ IDs 3069-3074 therein).

It can readily be seen that the inefficacy of the Norwegian OMV vaccine against strain 2996 (group 1) can be overcome by adding defined antigens from strain 2996. The results using NmB protein '287' are particularly good. The Norwegian vaccine can thus be improved without needing to prepare OMVs from a number of different strains.

This vaccine also offers protection against heterologous MenB strains. The same vaccines, prepared using 2996 strain proteins, was tested against five other strains. Titres were as follows:

| Group | 2996 | BZ133 | BZ232 | 1000 | MC58 | NGH38 |
|---|---|---|---|---|---|---|
| 1 | <4 | 1024 | <4 | >2048 | >2048 | 32 |
| 2 | 512 | 512 | <4 | >2048 | >2048 | 256 |
| 3 | 4096 | 4096 | 256 | 1024 | >2048 | 1024 |
| 4 | 1024 | 2048 | <4 | 2048 | >2048 | 64 |
| 5 | 256 | >32000 | <4 | >2048 | >2048 | 128 |
| 6 | 2048 | 2048 | 4 | <4 | 64 | 4 |
| 7 | 2048 | >32000 | 4 | 128 | 1024 | 128 |
| Control * | 32768 | 4096 | 8192 | 16384 | 16384 | 8192 |

* Controls: strains 2996, BZ133 & 1000 = OMVs prepared from homologous strain; strain BZ232 = OMVs prepared from 2996; MC58 & NGH38 = SEAM3

A second study supplemented 'Norwegian' OMVs with proteins from NmB strain 2996:
protein 919, expressed in E. coli without any fusion partner
ORF1, expressed in E. coli as a His-tagged fusion
Protein 287, expressed in E. coli as a GST fusion
A mixture of these three proteins, optionally with the NmC conjugate The preparations were adjuvanted with Al(OH)$_3$ and tested against the homologous strain using the bactericidal assay. Results were as follows:

|          | NmB  |       |        | NmC  |       |
|----------|------|-------|--------|------|-------|
| Antigen  | 2996 | NGH38 | 394/98 | C11  | BZ133 |
| OMVs     | <4   | 32    | 1024 * | <4   | 1024  |
| +919     | <4   | <4    | 4      | <4   | 512   |
| +ORF1    | 512  | 256   | 2048   | 4096 | 512   |
| +287     | 4096 | 1024  | 1024   | 512  | 4096  |
| +mix     | 1024 | 64    | 4      | 64   | 2048  |
| +mix +NmC | 256 | 128   | 2048   | 64000 | >32000 |

* the antibodies were bacteriostatic, not bactericidal

Further Work with Antigen 287

Combinations of Norwegian OMVs with antigen 287 were investigated further. 20 μg antigen 287 was combined with Norwegian OMP vaccine (15 μg OMP+Al(OH)$_3$) and used to immunise mice. The antibodies were tested in the bactericidal assay, and were effective against all strains tested. The results were as follows:

|          | NmB  |       |       |      |       |       |      | NmA   | NmC  |
|----------|------|-------|-------|------|-------|-------|------|-------|------|
| Antigen  | 2996 | BZ133 | BZ232 | 1000 | MC58  | NGH38 | NZ   | F6124 | C11  |
| OMVs     | <4   | 1024  | <4    | >2048 | 32768 | 32   | <4   | —     | —    |
| 287      | 8000 | 4096  | 256   | <4   | 512   | 2048  | 1024 | 1024  | 2048 |
| OMV + 287 | 4096 | 4096 | 256   | 1024 | 4096  | 1024  | 1024 | —     | —    |

In almost all cases, therefore, the combination of OMVs+ protein 287 surprisingly gives better results that the OMVs alone.

Recombinant OMVs

E. coli were transformed to express ORF1, ORF40 and ORF46. OMVs prepared from the recombinant E. coli were able to induce bactericidal antibodies against N. meningitidis. ORF1, ORF40 and ORF46 (strain 2996) were expressed as His-tagged fusions in E. coli and were prepared either as pure proteins or in the form of OMVs. Bactericidal titres against both preparations were tested using strain 2996 as challenge:

| Antigen:  | ORF1 | ORF40 | ORF46  |
|-----------|------|-------|--------|
| Purified  | 64   | 2048  | 16000  |
| OMV       | 1024 | 256   | 128000 |

Bactericidal titres using heterologous challenge strains were also measured. ORF46 gives a titre against strain MC58 of 4096 in pure form, but this rises to 32000 when in the form of OMVs. ORF1 gives a titre against NmA strain F6124 of 128 in pure form, but this rises to 512 when in the form of OMVs. ORF40 gives a titre against strain MC58 of 512 in pure form, but this doubles when in the form of OMVs.

These data show that NmB antigens retain immunogenicity when prepared in E. coli as OMVs and, furthermore, that immunogenicity can actually be enhanced.

It will be understood that this application describes the invention by way of example only and modifications may be made whilst remaining within the scope and spirit of the invention.

The invention claimed is:

1. A composition comprising a *Neisseria meningitidis* serogroup B outer membrane preparation mixed with a purified m741.pep protein comprising the amino acid sequence of SEQ ID NO: 22 or an immunogenic fragment of the m741.pep protein comprising ten or more consecutive amino acids of the amino acid sequence of SEQ ID NO: 22.

2. The composition of claim 1, wherein the protein, the *Neisseria meningitidis* serogroup B outer membrane preparation, or both are adsorbed on Al(OH)$_3$.

3. The composition of claim 1, wherein the outer membrane preparation comprises outer membrane vesicles (OMVs) of the *Neisseria meningitidis* serogroup B.

4. The composition of claim 3, wherein the OMVs are a deoxycholate extract from the *Neisseria meningitidis* serogroup B.

5. The composition of claim 2, wherein the protein is adsorbed on Al(OH)$_3$.

6. The composition of claim 1, further comprising an isolated or purified *Neisseria meningitidis* protein selected from the group consisting of:
   (a) protein ORF1 comprising the amino acid sequence of SEQ ID NO: 16;
   (b) protein ORF40 comprising the amino acid sequence of SEQ ID NO: 17;
   (c) protein ORF46 comprising the amino acid sequence of SEQ ID NO: 18;
   (d) protein 287 comprising the amino acid sequence of SEQ ID NO: 19;
   (e) protein 919 comprising the amino acid sequence of SEQ ID NO: 21 and
   (f) transferrin binding protein B (TbpB) comprising the amino acid sequence of SEQ ID NO: 15.

7. The composition of claim 6, comprising the protein ORF1 comprising the amino acid sequence of SEQ ID NO: 16.

8. The composition of claim 6, comprising the protein ORF40 comprising the amino acid sequence of SEQ ID NO: 17.

9. The composition of claim 6, comprising the protein ORF46 comprising the amino acid sequence of SEQ ID NO: 18.

10. The composition of claim 6, comprising the protein 287 comprising the amino acid sequence of SEQ ID NO: 19.

11. The composition of claim 6, comprising the protein 919 comprising the amino acid sequence of SEQ ID NO: 21.

12. The composition of claim 6, comprising the TbpB comprising the amino acid sequence of SEQ ID NO: 15.

13. A composition comprising a *Neisseria meningitidis* serogroup B outer membrane preparation isolated from a recombinant serogroup B *Neisseria meningitidis* that hyperproduces a protein from a strain of *Neisseria meningitidis* serogroup B different from the recombinant serogroup B *Neisseria meningitidis* and wherein the protein is m741.pep comprising the amino acid sequence of SEQ ID NO: 22 or an immunogenic fragment of the m741.pep protein comprising ten or more consecutive amino acids of the amino acid sequence of SEQ ID NO: 22.

14. The composition of claim 13, wherein the outer membrane preparation comprises outer membrane vesicles (OMVs) of the *Neisseria meningitidis* serogroup B.

15. The composition of claim 14, wherein the OMVs are an isolated deoxycholate extract from the recombinant *Neisseria meningitidis* serogroup B.

16. The composition of claim 13, wherein the *Neisseria meningitidis* serogroup B outer membrane preparation is adsorbed on Al(OH)$_3$.

17. The composition of claim 13, further comprising an isolated or purified *Neisseria meningitidis* protein selected from the group consisting of:
- (a) protein ORF1 comprising the amino acid sequence of SEQ ID NO: 16;
- (b) protein ORF40 comprising the amino acid sequence of SEQ ID NO: 17;
- (c) protein ORF46 comprising the amino acid sequence of SEQ ID NO: 18;
- (d) protein 287 comprising the amino acid sequence of SEQ ID NO: 19;
- (e) protein 919 comprising the amino acid sequence of SEQ ID NO: 21 and
- (f) transferrin binding protein B (TbpB) comprising the amino acid sequence of SEQ ID NO: 15.

\* \* \* \* \*